(12) United States Patent
Hoganson et al.

(10) Patent No.: US 8,795,242 B2
(45) Date of Patent: Aug. 5, 2014

(54) RESORBABLE POLYMERIC DEVICE FOR LOCALIZED DRUG DELIVERY

(75) Inventors: David M. Hoganson, St. Louis, MO (US); Gino Bradica, Ewing, NJ (US); Scott M. Goldman, Downingtown, PA (US); John H. Brekke, Duluth, MN (US)

(73) Assignee: Kensey Nash Corporation, Exton, PA (US)

( * ) Notice: Subject to any disclaimer, the term of this patent is extended or adjusted under 35 U.S.C. 154(b) by 1292 days.

(21) Appl. No.: 11/056,879

(22) Filed: Feb. 12, 2005

(65) Prior Publication Data

US 2005/0177118 A1 Aug. 11, 2005

Related U.S. Application Data

(60) Continuation-in-part of application No. 10/830,267, filed on Apr. 21, 2004, now Pat. No. 7,963,997, which is a continuation of application No. 10/199,961, filed on Jul. 19, 2002, now abandoned, and a continuation-in-part of application No. 09/206,604, filed on Dec. 7, 1998, now Pat. No. 6,264,701, which is a division of application No. 08/242,557, filed on May 13, 1994, now Pat. No. 5,981,825.

(60) Provisional application No. 60/386,191, filed on Jul. 19, 2001.

(51) Int. Cl.
*A61M 37/00* (2006.01)

(52) U.S. Cl.
USPC .................................................. 604/288.01

(58) Field of Classification Search
USPC ........... 424/424; 604/288.01, 288.02–288.04, 604/11
See application file for complete search history.

(56) References Cited

U.S. PATENT DOCUMENTS

| | | | |
|---|---|---|---|
| 3,948,254 A * | 4/1976 | Zaffaroni | 128/833 |
| 4,186,448 A | 2/1980 | Brekke | |
| 4,282,351 A | 8/1981 | Muzzarelli | |
| 4,485,097 A | 11/1984 | Bell | |
| 4,520,821 A | 6/1985 | Schmidt et al. | |
| 4,642,120 A | 2/1987 | Nevo et al. | |
| 4,783,335 A | 11/1988 | Lipshitz | |

(Continued)

FOREIGN PATENT DOCUMENTS

| | | |
|---|---|---|
| EP | 0369034 | 5/1990 |
| EP | 0505634 | 9/1992 |

(Continued)

OTHER PUBLICATIONS

Aviles, MD, Ronnier J., et al., "Inflammation as a Risk Factor for Atrial Fibrillation", *Circulation, 108*, (2003),3006-3010.

(Continued)

*Primary Examiner* — Quynh-Nhu H Vu
*Assistant Examiner* — Brandy S Lee
(74) *Attorney, Agent, or Firm* — Jeffrey R. Ramberg

(57) ABSTRACT

An implantable device for facilitating the healing of voids in bone, cartilage and soft tissue is disclosed. In one embodiment, the device is arranged for the local delivery of therapeutic agent. A preferred embodiment is a porous resorbable implant, wherein the therapy delivery may be localized in nature, rather than systemic, such that higher doses at the target site may be allowed than would be tolerable by the body systemically.

5 Claims, 5 Drawing Sheets

(56) References Cited

U.S. PATENT DOCUMENTS

| | | | |
|---|---|---|---|
| 4,853,225 A | 8/1989 | Wahlig et al. | |
| 5,010,167 A | 4/1991 | Ron et al. | |
| 5,041,138 A | 8/1991 | Vacanti et al. | |
| 5,071,656 A | 12/1991 | Lee et al. | |
| 5,110,604 A * | 5/1992 | Chu et al. | 424/484 |
| 5,133,755 A | 7/1992 | Brekke | |
| 5,152,791 A | 10/1992 | Hakamatsuka et al. | |
| 5,166,187 A | 11/1992 | Collombel et al. | |
| 5,268,178 A | 12/1993 | Calhoun et al. | |
| 5,294,446 A | 3/1994 | Schlameus et al. | |
| 5,306,311 A | 4/1994 | Stone et al. | |
| 5,356,429 A | 10/1994 | Seare | |
| 5,376,376 A | 12/1994 | Li | |
| 5,387,419 A | 2/1995 | Levy et al. | |
| 5,447,725 A | 9/1995 | Damani et al. | |
| 5,490,962 A | 2/1996 | Cima et al. | |
| 5,508,036 A | 4/1996 | Bakker et al. | |
| 5,512,600 A | 4/1996 | Mikos et al. | |
| 5,514,378 A | 5/1996 | Mikos et al. | |
| 5,632,727 A | 5/1997 | Tipton et al. | |
| 5,686,091 A | 11/1997 | Leong et al. | |
| 5,711,960 A | 1/1998 | Shikinami | |
| 5,723,331 A | 3/1998 | Tubo et al. | |
| 5,728,152 A | 3/1998 | Mirsch, II et al. | |
| 5,759,830 A | 6/1998 | Vacanti et al. | |
| 5,830,493 A | 11/1998 | Yokota et al. | |
| 5,876,452 A | 3/1999 | Athanasiou et al. | |
| 5,972,027 A * | 10/1999 | Johnson | 623/1.42 |
| 5,981,825 A | 11/1999 | Brekke | |
| 6,013,853 A | 1/2000 | Athanasiou et al. | |
| 6,136,024 A | 10/2000 | Shimizu | |
| 6,296,630 B1 | 10/2001 | Altman et al. | |
| 6,296,667 B1 | 10/2001 | Johnson et al. | |
| 6,306,169 B1 | 10/2001 | Lee et al. | |
| 6,306,424 B1 | 10/2001 | Vyakarnam et al. | |
| 6,350,284 B1 | 2/2002 | Tormala et al. | |
| 6,471,689 B1 * | 10/2002 | Joseph et al. | 604/892.1 |
| 6,471,983 B1 | 10/2002 | Veeger et al. | |
| 6,471,993 B1 | 10/2002 | Shastri et al. | |
| 6,482,184 B1 * | 11/2002 | Christensen et al. | 604/174 |
| 6,534,693 B2 | 3/2003 | Fischell et al. | |
| 6,551,618 B2 | 4/2003 | Baird et al. | |
| 6,635,049 B1 | 10/2003 | Robinson et al. | |
| 6,685,697 B1 | 2/2004 | Arenberg et al. | |
| 6,726,920 B1 * | 4/2004 | Theeuwes et al. | 424/423 |
| 6,726,923 B2 | 4/2004 | Iyer et al. | |
| 6,730,016 B1 | 5/2004 | Cox | |
| 6,748,653 B2 | 6/2004 | Lindemans et al. | |
| 2002/0007158 A1 * | 1/2002 | Burbank et al. | 604/288.03 |
| 2002/0115197 A1 * | 8/2002 | Ochi et al. | 435/287.1 |
| 2002/0150622 A1 | 10/2002 | Philbrook et al. | |
| 2002/0168338 A1 * | 11/2002 | Baird | 424/93.2 |
| 2003/0009145 A1 | 1/2003 | Struijker-Boudier et al. | |
| 2003/0113359 A1 * | 6/2003 | Iyer et al. | 424/423 |
| 2003/0147935 A1 * | 8/2003 | Binette et al. | 424/423 |
| 2004/0006146 A1 * | 1/2004 | Evans et al. | 521/50 |
| 2005/0261782 A1 | 11/2005 | Hoganson | |

FOREIGN PATENT DOCUMENTS

| | | |
|---|---|---|
| EP | 0544259 | 6/1993 |
| EP | 0784985 | 7/1997 |
| GB | 2175506 | 12/1986 |
| JP | 01-232967 | 9/1989 |
| RU | 2146136 | 3/2000 |
| WO | WO-93/15694 | 8/1993 |
| WO | WO-94/09722 | 5/1994 |
| WO | WO 95/11707 | 5/1995 |
| WO | WO 95/31157 | 11/1995 |

OTHER PUBLICATIONS

Halvorsen, MD, Per , et al., "The Effect of Dexamethasone on Side Effects After Coronary Revascularization Procedures", *Anesth Analg 2003, 96*, (2003),1578-83.

Mathew, MD, Joseph P., "A Multicenter Risk Index for Atrial Fibrillation", *JAMA, 291(14)*, (Apr. 14, 2005), 1720-1729.

Siden, Rivka , et al., "Epicardial Controlled-Release Verapamil Prevents Ventricular Tahcycardia Episodes Induced by Acute Ischemia in a Canine Model", *J Cardiovascular Pharmacology, 19*, Raven Press Ltd., New York, (1992),798-809.

Yared, MD, Jean-Pierre , et al., "Effects of Single Dose, Postinduction Dexamethasone on Recovery After Cardiac Surgery", *Ann Thorac Surg 2000, 69*, (2000),1420-1424.

* cited by examiner

RESORBABLE POLYMERIC DEVICE FOR LOCALIZED DRUG DELIVERY

CROSS REFERENCE

The present application is a continuation in part (CIP) of U.S. patent application Ser. No. 10/830,267, filed Apr. 21, 2004 which is a continuation of U.S. patent application Ser. No. 10/199,961, filed Jul. 19, 2002 and since abandoned, which is a continuation-in-part of U.S. patent application Ser. No. 09/909,027, filed Jul. 19, 2001 and since abandoned, which is a continuation-in-part of U.S. patent application Ser. No. 09/206,604, filed Dec. 7, 1998, now U.S. Pat. No. 6,264, 701, which is in turn a division of application Ser. No. 08/242, 557, filed May 13, 1994, now U.S. Pat. No. 5,981,825. The contents of each of the above-noted patents and applications is hereby fully incorporated herein by reference.

FIELD OF THE INVENTION

The present invention generally relates to the transport and/or culturing of cells, and more specifically to the healing of voids or other defects in bone, cartilage and soft tissue. The present invention also generally relates to providing the delivery of therapeutic agents. More specifically, the present invention provides for local delivery of the therapeutic agents by an implantable device, which agents can then be absorbed into the body.

BACKGROUND OF THE INVENTION

The medical repair of bones and joints and other tissue in the human body presents significant difficulties, in part due to the materials involved. Each bone has a hard, compact exterior surrounding a spongy, less dense interior. The long bones of the arms and legs, the thigh bone or femur, have an interior containing bone marrow. The material that bones are mainly composed of is calcium, phosphorus, and the connective tissue substance known as collagen.

Bones meet at joints of several different types. Movement of joints is enhanced by the smooth hyaline cartilage that covers the bone ends, by the synovial membrane that covers the hyaline cartilage and by the synovial fluid located between opposing articulating surfaces.

Cartilage damage produced by disease such as arthritis or trauma is a major cause of physical deformity and dehabilitation. In medicine today, the primary therapy for loss of cartilage is replacement with a prosthetic material, such as silicone for cosmetic repairs, or metal alloys for joint realignment. The use of a prosthesis is commonly associated with the significant loss of underlying tissue and bone without recovery of the full function allowed by the original cartilage. The prosthesis is also a foreign body which may become an irritating presence in the tissues. Other long-term problems associated with the permanent foreign body can include infection, erosion and instability.

The lack of a truly compatible, functional prosthesis subjects individuals who have lost noses or ears due to burns or trauma to additional surgery involving carving a piece of cartilage out of a piece of lower rib to approximate the necessary contours and inserting the cartilage piece into a pocket of skin in the area where the nose or ear is missing.

Surgical removal of infected or malignant tissue is disfiguring and can have harmful physiological and psychological effects. Regeneration of soft tissue, or tissue that mimics the natural properties of the removed tissue, can avoid or lessen these untoward consequences. Finally, a device which delivers a therapy could aid the regeneration of tissue, minimize risk of infection, and/or treat any underlying disease or condition.

The foregoing being exemplary, a device according to the teachings of the present invention is expected to add utility in many areas, see Table 1, which is meant to be expansive of the foregoing, and not limiting.

TABLE 1

Examples of tissues and procedures potentially benefiting from the teachings of the present invention Bone
Bone tissue harvest
Spinal arthrodesis
Spinal fixation/fusion
Osteotomy
Bone biopsy
Maxillofacial reconstruction
Long bone fixation
Compression fractures
Hip reconstruction/replacement
Knee reconstruction/replacement
Hand reconstruction
Foot reconstruction
Ankle reconstruction
Wrist reconstruction
Elbow reconstruction
Shoulder reconstruction
Cartilage
Mosaicplasty
Meniscus
Dental
Ridge augmentation
Third molar extraction
Tendon
Ligament
Skin
Topical wound
Burn treatment
Biopsy
Muscle
Dura
Lung
Liver
Pancreas
Gall bladder
Kidney
Nerves
Artery
Vein
Bypass Surgery
Cardiac catheterization
Heart
Esophagus
Mediastinum
Heart valve replacement
Partial organ removal In the past, bone has been replaced using actual segments of sterilized bone or bone powder or porous surgical steel seeded with bone cells which were then implanted. In most cases, repair to injuries was made surgically. Patients suffering from degeneration of cartilage had only pain killers and anti-inflammatories for relief.

Until recently, the growth of new cartilage from either transplantation or autologous or allogeneic cartilage has been largely unsuccessful. Consider the example of a lesion extending through the cartilage into the bone within the hip joint. Picture the lesion in the shape of a triangle with its base running parallel to the articular cavity, extending entirely through the hyaline cartilage of the head of the femur, and ending at the apex of the lesion, a full inch (2.54 cm) into the head of the femur bone.

Presently, there is a need to successfully insert an implant device which will assure survival and proper future differentiation of cells after transplantation into the recipient tissue defect. Difficulties have been experienced with engineering the implant environment such that cells may survive, and also with supporting proper cell differentiation.

Presently, for example, cartilage cells, called chondrocytes, when implanted along with bone cells, can degenerate or dedifferentiate into more bone cells. Because hyaline cartilage is an avascular tissue, it should be protected from intimate contact with sources of high oxygen tension such as blood. Bone cells, in contrast, require high oxygen levels and blood. For this reason, the subchondral bone region of the device should be isolated from the cartilage region, at least so far as oxygen and blood are concerned.

Most recently, two different approaches to treating articular lesions have been advanced. One approach such as disclosed in U.S. Pat. No. 5,041,138 is coating bioderesorbable polymer fibers of a structure with chemotactic ground substances. No detached microstructure is used. The other approach such as disclosed in U.S. Pat. No. 5,133,755 uses chemotactic ground substances as a microstructure located in voids of a macrostructure and carried by and separate from the biodegradable polymer forming the macrostructure. Thus, the final spatial relationship of these chemotactic ground substances with respect to the bioresorbable polymeric structure is very different in U.S. Pat. No. 5,041,138 from that taught in U.S. Pat. No. 5,133,755.

The fundamental distinction between these two approaches presents three different design and engineering consequences. First, the relationship of the chemotactic ground substance with the bioresorbable polymeric structure differs between the two approaches. Second, the location of biologic modifiers carried by the device with respect to the device's constituent materials differs. Third, the initial location of the parenchymal cells differs.

Both approaches employ a bioresorbable polymeric structure and use chemotactic ground substances. However, three differences between the two approaches are as follows.

I. Relationship of Chemotactic Ground Substances with the Bioresorbable Polymeric Structure The design and engineering consequence of coating the polymer fibers with a chemotactic ground substance is that both materials become fused together to form a single unit from structural and spatial points of view. The spaces between the fibers of the polymer structure remain devoid of any material until after the cell culture substances are added.

In contrast, the microstructure approach uses chemotactic ground substances and/or other materials, separate and distinct from the macrostructure. The microstructure resides within the void spaces of the macrostructure. Additionally, an embodiment incorporating a microstructure may use materials such as polysaccharides and chemotactic ground substances that are spacially separate from the macrostructure polymer thereby forming an identifiable microstructure, separate and distinct from the macrostructure polymer.

The design and engineering advantage to having a separate and distinct microstructure capable of carrying other biologically active agents can be appreciated in the medical treatment of articular cartilage. RGD attachment moiety of fibronectin is a desirable substance for attaching chondrocytes cells to the lesion. However, RGD attachment moiety of fibronectin is not, by itself, capable of forming a microstructure of velour in the microstructure approach. Instead, RGD may be blended with a microstructure material prior to investment within macrostructure interstices.

II. Location of Biologic Modifiers Carried by a Device with Respect to the Device's Constituent Materials Coating only the polymer structure with chemotactic ground substances necessarily means that the location of the chemotactic ground substance is only found on the macrostructure (e.g., bioresorbable polymer) fibers, thereby affording a two dimensional presentation. The microstructure approach uses the microstructure to carry biologic modifiers (e.g., growth factors, morphogens, drugs, etc.), however the presentation is analogous to a three dimensional presentation. Therefore, the coating approach has a limited capacity to carry biologic modifiers with the biodegradable polymeric structure.

III. Initial Location of the Parenchymal Cell

Because the coating approach attaches the chemotactic ground substances to the surfaces of the structure and has no microstructure resident in the void volume of the device, the coating approach precludes the possibility of establishing a network of extracellular matrix material, specifically a microstructure, within the spaces between the fibers of the polymer structure once the device is fully saturated with cell culture medium. The coating approach predetermines that any cells introduced via culture medium will be immediately attracted to the surface of the structure polymer and attach thereto by virtue of the chemotactic ground substances on the polymer's surfaces.

The consequence of confining chemotactic ground substances to only the surfaces of the polymeric structure places severe restrictions on the number of cells that can be accommodated by the coated device.

In contrast with the coating approach, the microstructure approach, by locating chemotactic ground substances in the void spaces of the device, makes available the entire void volume of the device to accommodate the attracted cells which then lay down their own extracellular matrix resulting in a more rapid and complete tissue regrowth or ingrowth.

One of the many objects of this invention, as will be discussed, is to protect and aid cellular ingrowth or regeneration of various types of new tissue, as well as providing methods of concurrent delivery of therapies and other treatments.

Another object of the present invention is the delivery of therapeutic drugs or biologically active agents from a device having the aforementioned macrostructure and microstructure. Such a device could be useful in preventing unwanted effects of various therapies (i.e., interventional surgical procedures, radionuclear therapies, drugs, etc.) For example, early postoperative atrial fibrillation (AF) is common following cardiac surgery, occurring in 25 to 35% of patients after coronary artery bypass grafting (CABG). Postoperative AF following cardiac or lung surgery can cause a number of complications, including congestive heart failure, stroke, and hemodynamic instability. It is responsible for increased hospital costs and prolonged hospitalization. This tachyarrhythmia usually occurs within one week following cardiac or lung surgery and generally resolves over the next three weeks without any long-term risk for recurrence. Previous studies have shown that the peak incidence of early postoperative AF is on the second postoperative day after coronary artery bypass grafting (CABG). Seventy percent of the patients who had AF following CABG experienced this arrhythmia within the first three days postoperatively. Moreover, the incidence of early postoperative AF varies depending on the type of procedure, being highest in patients having valvular surgery with or without CABG. Off-pump CABG has been associated with a lower incidence of AF than traditional on-pump CABG.

The precise etiology of atrial fibrillation is unclear. Some studies have shown that an increased inflammatory response correlates with the occurrence of early postoperative AF. It has been shown that elevated C-reactive protein is associated with the occurrence of AF. It has been reported that anti-inflammatory therapy significantly reduced the incidence of early postoperative AF following cardiac surgery. Yared and colleagues [Yared, Starr, Torres, et al., Effect of Single Dose, Post-induction Dexamethasone on Recovery After Cardiac Surgery, Ann. Thorac. Surg. 69:1420-1424 (2000)] demonstrated that patients receiving corticosteroid therapy had a significantly lower incidence of postoperative AF following both CABG and valvular surgery than patients that did not receive corticosteroid therapy. Matthew and colleagues [Matthew, Fontes, Tudor et al., A Multicenter Risk Index for Atrial Fibrillation After Cardiac Surgery, JAMA 291:1720-1729 (2004)] found that administering non-steroidal anti-inflammatory medication was associated with a reduction in the odds of developing postoperative atrial fibrillation, suggesting that inflammation may contribute to the pathogenesis of postoperative atrial fibrillation.

It has recently been found that systemic delivery of anti-inflammatory medications have reduced the incidence of AF following cardiac surgery. However, there are significant drawbacks of using systemic anti-inflammatory medication following cardiac surgery. For example, non-steroidal anti-inflammatory medication can have detrimental effects on renal function and steroidal anti-inflammatory medication can impair wound healing and reduce the immune response. It is desirable to overcome these limitations of systemic delivery of anti-inflammatory agents by locally delivering them to the desired tissue, namely the heart and great vessels and achieve the desired local tissue concentration while minimizing or limiting exposure of these agents to other tissues within the body. The discovery of the present invention allows local delivery of these types of drugs on a local scale, affording the beneficial effect of the drug on the target site, and further avoiding the drawbacks of delivery on a systemic scale.

Zaffaroni in U.S. Pat. No. 3,948,254 describes an implantable or insertable drug delivery device wherein a drug carrier material is enclosed in a microporous surrounding wall, to provide for extended drug release from the drug carrier material as the drug diffuses through the microporous surrounding wall.

Levy et al. in U.S. Pat. No. 5,387,419 describe a biodegradable implant suitable for localized drug delivery. The implant is prepared as a polymer/solvent and drug coating that polymerizes in situ to form a coating or film that serves to elute the drug.

Altman et al. in U.S. Pat. No. 6,296,630 describe a drug delivery system, wherein a "patch" for drug delivery is applied directly against the heart, wherein the drug to be delivered is renewable by accessing an implanted port in fluid communication with the patch.

Lindemans in U.S. Pat. No. 6,748,653 describes a drug delivery and defibrillator pad, wherein a defibrillator pad having a defibrillating lead is placed against the heart, and the pad is further arranged to deliver a drug to the heart. Lindemans described the pad as being biodegradable.

Cox in U.S. Pat. No. 6,730,016 describes a jacket that may be placed around all or a portion of the heart to constrain the heart from overexpansion. The jacket may have reinforcing ribs to provide structure to the jacket, and the material may be limited in its ability to expand, thereby preventing harm to the organ. The jacket may be capable of localized drug delivery.

Theeuwes in U.S. Pat. No. 6,726,920 describes an implantable patch for drug delivery having an impermeable outside layer and a permeable inside layer, such that a drug reservoir contained between the two layers is arranged to deliver a drug by diffusion through the permeable inside layer.

SUMMARY OF THE INVENTION

A device of the present invention is a prosthesis or implant for in vivo culturing of tissue cells in a diverse tissue or homogeneous lesion, or for non-systemic delivery of one or more therapeutic agents to a target tissue of a living being. The entire macrostructure, or a major portion, of this device may be composed of a bioresorbable polymer. Alternatively, the microstructure may be the only portion of the device which is resorbable, if a microstructure was employed at all. Alternatively, it is also conceived that the device could be used to culture cells via in vitro techniques known in the art for later in vivo transplantation.

A device of the present invention may include a macrostructure, microstructure, free precursor cells cultured in vitro or from tissue, or biologically active agents. "Biologically active agents" as used in this disclosure meaning, but not limited to, growth factors, morphogens, drugs, proteins, cells, cellular components, signaling proteins, signal transduction factors, and other therapeutic agents.

In a first major aspect of the present invention, an anatomically specific device could be designed primarily for treating cartilage and bone lesions and, when used for that purpose, preferentially has two main regions: a cartilage region and a subchondral bone region. Alternatively, it is envisioned that a singular region may be employed to repair defects in other areas and types of host tissue. Likewise, additional regions may be used to "bridge" tissue of distinct histological variation, as well as other variations.

A first embodiment of this aspect of the present invention comprises a cartilage region which has a macrostructure and a microstructure. The selective concentration gradient of material in the microstructure may be selectively varied within certain regions of the macrostructure voids to affect different biologic characteristics and tissue requirements.

The microstructure of a single device of the present invention may be composed of multiple different materials, some without chemotactic properties, in different regions of macrostructure void space depending upon varying tissue and biologic characteristics and requirements.

The subchondral bone region of this embodiment includes a macrostructure composed of a biologically acceptable, polymer (preferably bioresorbable) arranged as a one piece porous body with "enclosed randomly sized, randomly positioned and randomly shaped interconnecting voids, each void communicating with all the others, and communicating with substantially the entire exterior of the body" (quoted portion from U.S. Pat. No. 4,186,448). In the preferred embodiment as described here, the internal three-dimensional architecture of the macrostructure resembles that of cancellous bone. In other embodiments, the internal 3-D architecture of the macrostructure may be highly ordered, as described in U.S. Pat. No. 5,981,825, to replicate the spatial patterns of other tissues or to create a tissue pattern required for performance of specific anatomic and/or physiologic functions. In one preferred embodiment, polylactic acid (PLA), fabricated in the 3-D architecture of intercommunicating voids described above forms the macrostructure. Other members of the hydroxy acid group of compounds can also be used as can any bioresorbable polymer, natural or synthetic, if fabricated into a similar architecture. Alternatively, the macrostructure could be fabricated from natural materials (e.g., bone, coral, or collagen), ceramic materials (whether natural or synthesized, e.g., hydroxyapatite or tricalcium phosphate), or other materials, such as those shown in Tables 2 and 3.

The gross, or macro, structure of this embodiment attempts to address three major functions for chondrogenesis and osteogenesis: 1) restores mechanical architectural and structural competence; 2) provides biologically acceptable and mechanically stable surface structure suitable for genesis, growth and development of new non-calcified and calcified tissue; and 3) functions as a carrier for other constituents of the present invention which do not have mechanical and structural competence.

The microstructure of this embodiment may be composed of various polysaccharides which, in a preferred form, is alginate but can also be hyaluronic acid (abbreviated by HY). Interstices of the polylactic acid macrostructure of the body member are invested with the microstructure substance which may be in the form of a velour having the same architecture of interconnecting voids as described for the macrostructure, but on a microscopic scale. Functions of the microstructure (e.g., HY) may include: 1) attraction of fluid blood throughout the device; 2) chemotaxis for mesenchymal cell migration and aggregation; 3) carrier for osteoinductive and chondro-inductive agent(s); 4) generation and maintenance of an electronegative wound environment; 5) agglutination of other connective tissue substances with each other and with itself; and 6) coating of the edges of the macrostructure to minimize or prevent foreign body giant cell responses, as well as other adverse responses to the implant. Other examples of suitable microstructures are fibronectin and, especially for the reconstruction of articular cartilage, an RGD attachment moiety of fibronectin.

The osteoinductive agent, bone morphogenetic protein, has the capacity to induce primitive mesenchymal cells to differentiate into bone forming cells. Another osteogenic agent, bone derived growth factor, stimulates activity of more mature mesenchymal cells to form new bone tissue. Other biologically active agents which can be utilized, especially for the reconstruction of articular cartilage, include but are not limited to transforming growth factor beta (TGF beta) and basic fibroblast growth factor (bFGF).

In this first embodiment, as well as the balance of the specification and claims, the term "bioabsorbable" is frequently used. There exists some discussion among those skilled in the art, as to the precise meaning and function of bioabsorbable material (e.g., polymers), and how they differ from resorbable, absorbable, bioresorbable, biodegradable, and bioerodable materials. The current disclosure contemplates all of these materials, and combines them all as bioresorbable. Any use of an alternate disclosed in this paragraph is also meant to describe and include all of the others.

In a second embodiment of the present invention, the device acts as a transport device for precursor cells harvested for the production of connective tissue. The device can be press fit into the site of lesion repair, and subsequently charged with a solution of cells, growth factors, etc., as will be described later. Another aspect of this embodiment is that the microstructure velour can be treated with an RGD attachment moiety of fibronectin that facilitates the attachment of free precursor cells to be carried to the lesion repair site.

Additional embodiments of the present invention allow for the tailoring of mechanical and physical properties through the use of additions of other polymers, ceramics, microstructures and processes (e.g., void tailoring, cross-linking, and pre-stressing). Additionally, the delivery of therapies aids regeneration of tissue, minimizes procedural discomfort to the patient, and treats underlying disease.

A second major aspect of the present invention focuses on delivering one or more therapeutic agents to a "targeted tissue", and preferably in a non-systemic manner. In accordance with one preferred embodiment of this second major aspect of the invention, the construct described herein allows delivery of a therapeutic agent to the heart and, when applicable, the great vessels. At least a portion of the construct may be directly applied to the surface of the heart. The therapeutic agent is released into the surface of the heart by the construct. The therapeutic agent may then be absorbed by the heart tissue. The therapeutic agent elicits a beneficial effect on the heart or its surrounding structures. The therapeutic agent may prevent inflammation and, or prevent the development or continuation of cardiac arrhythmias.

In accordance with one preferred embodiment of this aspect of the invention, the construct may be resorbable and deliver the therapeutic agent to the heart by releasing the agent as the construct is resorbed.

In a preferred embodiment of this aspect of the invention, the construct may release the therapeutic agent by diffusion through the construct or by a selective portion of the construct designed to control release of the therapeutic agent.

In accordance with one preferred embodiment of this aspect of the invention, a portion of the construct may lie outside the chest. The construct may also have a portion that stores therapeutic agent and a portion that delivers the agent to the heart. A portion of the storage component of the construct may lie away from the immediate surface of the heart and be the component that may lie outside the chest.

Various of these preferred embodiments may deliver one or more therapeutic agents to the heart. The construct may deliver an agent that prevents inflammation such as a steroid and may subsequently, or simultaneously deliver another agent such as an anti-chemotactic agent. The construct may deliver varying amounts of the therapeutic agent(s) at different times. For example, a larger dose of a therapeutic agent may be initially delivered, while a lower dose is then delivered over an extended time. This complex and varied delivery may be accomplished by utilizing a construct that has a porous structure where therapeutic agent(s) may be incorporated within the structure and within the pores. The use of resorbable polymer with various resorption times may also be used to control the delivery of said agents. Microspheres may be used by the construct or released by the construct. A therapeutic agent(s) may be delivered using said microspheres.

In accordance with one preferred embodiment of this aspect of the invention, the construct may deliver a therapeutic agent to a tissue other than the heart. The construct may be pre-shaped or may be modified to conform to a variety of tissues. The therapeutic agent delivery construct may be very flexible so it can be positioned adjacent to tissues that lie in one or more plane. As an example, the construct may be used to locally delivery chemotherapeutic or other therapeutic agents into tissue(s).

In accordance with one preferred embodiment of this aspect of the invention, the construct may be delivered to the site of the tissue with minimally invasive techniques, such as with needle, catheter based delivery systems, laproscopic or robotic surgery, or it may also be delivered via open surgery.

These various embodiments may be adaptable to various surgical and medical applications, and the examples herein are not meant to be limiting but rather illustrative.

BRIEF DESCRIPTION OF THE DRAWINGS

Other aspects and many of the attendant advantages of this invention will readily be appreciated as the same becomes better understood by reference to the following detailed description when considered in connection with the accompanying drawings wherein.

DESCRIPTION OF THE PREFERRED EMBODIMENTS

Figure 1:
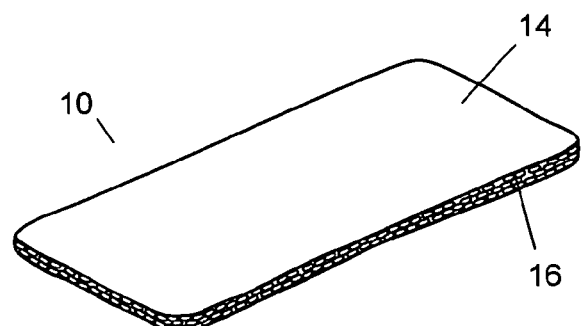
FIG. 1 is an isometric view of an embodiment of the construct.

Before the various embodiments and features and benefits are described, it is to be understood that this invention is not intended to be limited to the particular constructs and methods described in the preferred embodiments, as one skilled in the art can extend the concepts involved using variations which are obvious after reading the present disclosure.

It must be noted that, as used in this specification and the appended claims, the singular forms "a", "an", and "the" include plural referents, unless the context clearly dictates otherwise.

Unless defined otherwise, all technical and scientific terms used herein have the same meaning as commonly understood by one of ordinary skill in the art to which this invention belongs. Although any methods and materials similar or equivalent to those described herein may be useful in the practice or testing of the present invention, preferred compositions, films, methods and materials are described below.

In an embodiment, a device and methods according to the preferred teachings of the present invention are disclosed for treating mammalian bone and cartilage and soft tissue deficiencies, defects, voids and conformational discontinuities produced by congenital deformities, osseous and/or soft tissue pathology, traumatic injuries, and accidental, surgical, or functional atrophy. In a first aspect of the invention, the primary purpose of this implant device is to provide the means by which chondrocytes, or other cells, and their attendant synthesis, cultured in vitro, can be transported into a defect and be safely established therein. Thus, the most preferred embodiments of the present invention provides means to regenerate a specific form of tissue. A second aspect of the invention, to be discussed in more detail later, focuses on the ability of the implant device to deliver one or more therapeutic agents to a specific region of a living being, and preferably in a non-systemic manner.

Referring for the moment to the first aspect of the invention, a first embodiment of the present invention consists of two main parts, the cartilage region and the subchondral bone region joined at an interface surface. Each of the cartilage and the subchondral bone regions of the device includes a macrostructure composed of a bioresorbable polymer either as homogeneous polymers or combinations of two or more co-polymers from groups of, for example, poly (alpha-hydroxy acids), such as polylactic acid or polyglycolic acid or their co-polymers, polyanhydrides, polydepsipeptides, or poly- orthoester. Devices fabricated for prototypes of animal studies to-date have been fabricated from the homopolymer D, D-L, L-polylactic acid, and polyelectrolytic complexes.

The bioresorbable polymer in the subchondral bone region in this form is in the architecture of cancellous bone such as of the type described in U.S. Pat. Nos. 4,186,448 and 5,133,755, which are hereby incorporated herein by reference.

The architecture of the cartilage region may be formed utilizing established techniques widely practiced by those skilled in the art of bioresorbable polymers. These methods include injection molding, vacuum foaming, spinning hollow filaments, solvent evaporation, soluble particulate leaching or combinations thereof. For some methods, plasticizers may be required to reduce the glass transition temperature to low enough levels so that polymer flow will occur without decomposition.

The macrostructure polymer of the cartilage region is joined or bound to the macrostructure polymer of the subchondral bone region by a process such as heat fusion which does not involve the use of solvents or chemical reactions between the two polymer segments. The resulting union between the two architectural regions is very strong and can withstand any handling required to package the device as well as any forces delivered to it as a result of the implantation technique without distorting the device's internal architecture of void spaces.

In former constructs such as U.S. Pat. No. 5,133,755, the preferred microstructure was hyaluronan which is synonymous with hyaluronic acid, hyaluronate, HA and HY. The hyaluronan was distributed uniformly throughout the internal void volume of the device. According to the teachings of the present invention, an option is provided of selecting whether or not the microstructure, if any, should be dispersed throughout all the void spaces depending on whether the arrangement is beneficial to the tissues being treated. A device of the present invention permits incomplete dispersal as desired or complete dispersal throughout the entire void volume of the device but expressing concentration gradients of microstructure material as a means of controlling transplanted cell population numbers within the device's internal domains.

A dry filamentous velour of chemotactic ground substance, for example RGD attachment moiety of fibronectin carried by hyaluronic acid or alginic acid velour, may be established within the void spaces of the device. Upon saturation with water, water-based cell culture media or fluid blood, the dry velour of chemotactic ground substance is dissolved into a highly viscous gel which maintains the chemotactic ground substance as a network of dissolved polysaccharide strands, still suspended within the void volume of the polymeric macrostructure. It is envisioned that other therapies may also be carried by this gel, as will be discussed later.

If the cell culture media is a fluid which saturates the device and creates the gel, then those cells suspended in the culture medium will be temporarily trapped within the gel due to the gel viscosity. The degree of gel viscosity and the length of time the gel maintains significantly high viscosities will aid in cellular propagation, i.e., restraining the transported cells by means of microstructure gel gives the cells additional time to execute biological processes. Additionally, this restraint can be used to modulate the delivery rate of the therapy.

The volume of space once occupied by the microstructure gel can then be occupied by the interstitial fluid and increased numbers of cells. In the articular cartilage regeneration of the preferred form, it is desired to protect the transplanted cells from access to fluid blood and collateral circulation. In other tissue regeneration situations, however, it may be desirable or beneficial to attract fluid blood into the device's interstices as quickly as possible. In these situations, therefore, fibrin (i.e. blood clot), endothelial cells, or other materials or therapies may be loaded into the device, or gained from sources of viable collateral circulation.

Certain embodiments of the present invention depart from prior practice by strategically positioning the microstructure material in that specific portion of the device which performs particular functions unique to the mature anatomy being regenerated in that vicinity. Such segregation of microstructure material within the device is based on the need to endow one portion of the device with special biologic functions that should be isolated from the remainder of the implanted device.

In yet another embodiment of the present invention, the microstructure has a secondary purpose to present enough chondrocytes to the subchondral bone region immediately adjacent to the cartilage region to insure that a competent osteo-chondral bond is established between the newly developed cartilage and the newly developed bone.

Within the inventive concept of several embodiments of the present invention is the establishment of variations in the concentration of microstructure within the void space network of the macrostructure in order to assure that the therapeutic elements and biologically active agents brought from in vitro culture, or loaded as will be described later, are present within the final device in greatest quantity where they are most needed. Such variations in concentration can be accomplished by varying concentrations of microstructure solutions prior to investment into macrostructure voids of the device or regions thereof before joining, as well as other methods known in the art.

In yet another embodiment of the current invention, the cartilage region of the construct comprises a polyelectrolytic complex (PEC). This complex preferably comprises polyanions and polycations. Since certain of these complexes in their dry states may not have sufficient strength to allow handling, processing may be required to increase their structural integrity. This processing can follow the methods previously disclosed, as well as various other generic techniques known to those skilled in the art. Because of the unique bonding structures contained in PEC's, some researchers have referred to them as poly-ionic complexes (PIC's). For this reason, the current disclosure recognizes no difference between the PEC and the PIC.

The PEC may be formed from glycosaminoglycans (GAG's) and polycations as well as other similarly structured compounds. While having the requisite electron affinity noted above for bonding, some of the sulfonated GAG's may not be effective in attracting the appropriate cell-types. In a preferred embodiment, the PEC is made from hyaluronic acid (HY), a non-sulfonated GAG, and chitosan. The PEC may be fabricated by various methods known to those skilled in the art, one such method follows.

The strong negative charge associated with HY is provided by the carboxylic acid group (—COOH) of its glucuronic acid moiety. When exposed to pH levels below about 6.5, the amine groups of chitosan molecules become protonated, thus rendering the molecules soluble in water and providing them with a strong positive charge that attracts negatively-charged molecules (e.g., HY, etc.) and thus forming electrostatic interactions. When a solution of protonated chitosan is exposed to a solution of HY, an insoluble precipitate (the PEC) is formed.

In yet another PEC embodiment, the PEC is made from hyaluronic acid and collagen (i.e., collagen type I or type II or type III, etc.), where collagen acts as a polycation. Collagen, an amphoteric species, functions as a cation when treated similarly to chitosan, as described above, or by other methods known to those skilled in the art.

The collagen may be supplied to the PEC in the form of demineralized bone matrix (DBM) material. It is realized that DBM also comprises, in addition to collagen, morphogens and growth factors, as secondary constituents. It is also recognized that these secondary constituents may add to the overall tissue regenerative capacity of the implant.

Other glycosaminoglycans such as, but not limited to, heparin, chondroitin-4-$SO_4$, chondroitin-6-$SO_4$, dermatan-$SO_4$, and keratin sulfate may also be used as a complement to or in place of hyaluronic acid, in these various embodiments.

In a similar embodiment, the macrostructure or microstructure, if any, of any region(s) may comprise chitosan, not bound in the aforementioned PEC. This embodiment, herein referred to as a "regeneration complex" may be formed by the techniques discussed herein, as well as those others known in the art. Alternatively, this regeneration complex may comprise a protein (e.g., type I collagen, type II collagen, type III collagen, carrageenan, fibrin, elastin, resilin, abductin, demineralized bone, or agarose), polysaccharide (e.g., cellulose, starches, chitosan, alginate, sulfated glycosaminoglycans, or non-sulfated glycosaminoglycans), a lipid (e.g., phospholipid, triglyceride, waxes, steroids, prostaglandins, or terpenes), a synthetic polymer (e.g., polylactide, polyglycolide, polyurethane, polyethylene, poly-e-caprolactone, polyvinyl alcohol, polycarbonate, or PTFE), ceramic (e.g., bioglass or calcium phosphate), singularly or as a mixture thereof. These alternatives may be formed by methods similar to those used for monolithic chitosan, as well as those previously disclosed.

By way of example, one embodiment utilizes a resorbable polymer macrostructure and hyaluronic acid microstructure in one region that is adjacent to a collagen regeneration complex. The collagen can be of several varieties as well as composites of thereof. Kensey Nash Corporation (Exton, Pa.) manufactures soluble collagen known as Semed S, fibrous collagen known as Semed F, and a composite collagen known as P1076. Each of these materials would be suitable for this embodiment. This embodiment may also include additives (e.g., sodium hyaluronate) blended or composited with the collagen slurry and co-lyophilized to create a material with desirable mechanical and chemical properties. The regeneration complex may undergo chemical, thermal, or radiation treatments in order to cross-link the material to provide desired strength and/or degradation qualities. Additionally, a calcium mineral such as hydroxyapatite or a growth factor, such as TGF-beta, may be added to the regeneration complex or to the neighboring region(s) in order to customize the implant for use in a bone or cartilage regeneration device. All of the foregoing alterations of the device's mechanical, chemical, or biological properties and responses are referred to as "matrix matching."

Matrix matching may also be achieved by processes other than cross-linking. For example, pore size, shape, and population may be engineered, by degree and rate of lyophilization, the polymer structure may be plastically strained or directionally treated to impart anisotropy or the like. As has been described, macrostructure and microstructural additions can greatly affect the degree of matrix matching; not only by the properties of addition (i.e., relative to the properties of the host matrix), but also by the relative amount placed therein (i.e., relative to total amount of macrostructure, or total amount of void space available to be filled by the microstructure).

Such matrix matching may be employed to approximate or nearly approximate the property of the host or other desired tissue to be regenerated. Alternatively, where the aforementioned result is not feasible, desirable (e.g., due to patient discomfort, allowances for inflammation of existing tissue, or sacrificing some strength for added toughness), or practical, the degree of matrix matching may be intentionally limited. While several exemplary embodiments have been given, additional composite elements and additives are contemplated (e.g., including PEC complexes and regeneration complexes, and combinations thereof), many of which are listed in Tables 2 and 3. Various other processes are also known in the art, which may be used alone, or in combination with any of the foregoing, in order to accomplish this same effect and result.

The tissue resulting after ingrowth or regeneration may also be matrix matched, that is, the tissue strength, density, and pliability may be altered by the matrix used. Ideally, the device would be matrix matched, and so would the regenerated tissue, although matrix matching refers to either, as is discussed in more detail later.

Another similar embodiment utilizes a demineralized bone matrix macrostructure and hyaluronic acid microstructure in one region that is adjacent to a chitosan PEC, as is described above, on a first side and a chitosan PEC on a second diametrically opposed side. This multi-layered implant would have the ability to regenerate cancellous bone through its middle region while regenerating cortical bone or cartilage on the end regions. Bone or cartilage are used in this example, but various other tissues are contemplated, and the regions may be arranged other than uniaxially. Additionally, an embodiment is contemplated wherein the demineralized bone may be replaced with porous hydroxyapatite if a stronger implant or longer-lasting type implant is desired.

In yet another embodiment, collagen may be used, for example, in the form of a porous fabric, to define a macrostructure. The porous fabric can be created to allow for specific pore size and separation. The fabric maintains an architecture that is suitable and similar to the atmosphere that chondrocytes are exposed to in host tissue. This macrostructure presents the structural integrity necessary to supply a homeostatic atmosphere for chondrocyte viability. This allows regenerative cascades to occur and allows for replication of damaged tissue. In addition, elements may be added to the macrostructure to create one microstructure. An example of this can be hyaluronic acid, demineralized bone matrix DBM, etc. Regardless of whether or not a microstructure is used, the macrostructure region may be attached to a second region via a porous polymeric film.

This film may be interposed between the first (e.g., collagen) and second regions at their interface, thereby increasing the strength of the bond. This interposition may be formed in a manner similar to the following example; a porous or non-porous film may be created of the desired polymer to create the needed bond. The thin film may be placed between the two regions to allow fixation in such manner where heat, UV, etc. may be used to combine the two materials.

Additionally, the polymer film may be constructed with the use of a solvent to create the film. This solution/slurry/suspension/gel emulsion can be applied to both or either material, with varying concentrations to bind the two materials. An example of one such procedure would be to apply the solution in such a fashion where a brush would be used for application. By way of example and not limitation, other manners may be employed, including spraying, dipping, etc. Therefore, these embodiments describe the application of the film in the liquid and/or solid states, and this disclosure contemplates other methods of polymer deposition known to those skilled in the art (e.g., spraying, dipping, heat application, UV, etc.).

In the foregoing PEC and regeneration complex embodiments, it is also contemplated that these devices will be implanted into a tissue requiring regeneration of one or multiple tissues. The devices of this disclosure may be implanted in a variety of ways. In one embodiment, the implant will be pressed into a defect site and, as will be discussed later in greater detail, will expand in apparent volume thus maintaining positive contact with host tissue. Other methods of implantation include suturing the implant into place, suturing a flap over the implant (such as a periosteal flap), using a glue or sealant (such as a fibrin glue), screws and fixturing, containing the implant within a separate device which is screwed, glued (e.g. thrombin, cyanoacrylate, etc.), press-fitting in place (such as an interbody fusion cage), or by other methods known to those skilled in the art.

Additionally, the shape or contouring of the implant can be used to hold the implant in place. In one embodiment, the implant may be created in the shape of a screw or a barb by using a mold, by cutting away the material, or by other methods known to those skilled in the art. In another embodiment, the contouring is created only in a region of the implant where tissue will regenerate the fastest. The contouring is purposely designed to provide resistance to shear, tensile, compressive, torque, and other forces acting to dislodge the implant. While some applications require contouring in only one region, other applications will require multiple regions of contouring.

The foregoing PEC and regeneration complex embodiments will have certain beneficial reactions following implant. That is, among other things, particular of these formations will imbibe water-based fluids in the implant vicinity. This fluid infusion will cause one or more regions of the implant to swell. Swelling may be important for securement reasons, as previously discussed, or for its affect on biological activity.

The swelling of these particular implant compositions is nearly equiaxial, that is, proportional in all directions to dimensions of the original, dry construct. Upon prolonged hydration, void spaces of the dry construct become occluded by the gel generated when water becomes bound to fibers of the PEC and additional water becomes entrapped between hydrated PEC filaments. Thus, those skilled in the art refer to this resulting structure as a hydrogel. The hydrogel medium endows its region of the device with several benefits that include, but are not limited to: (i) restricting trans-implant communication of biologically active agents; (ii) allowing its cargo of biologically active agents unrestricted access to host tissues immediately after implantation while progressively restricting this access over time; (iii) providing a depot of biologically active agent for access by cells entering the hydrogel region; and (iv) establishing the early microenvironment for cell migration into the defect (e.g., chemotaxis). The minimization of the access to these agents, however, is not detrimental to the function of the implant, since mass transfer (i.e., transfer of gases, nutrients, and cell waste products) occurs through hydrogels, and the cellular functions of respiration and metabolism continue.

In the foregoing PEC and regeneration complex embodiments, it is contemplated that the subchondral bone region comprises a resorbable polymer (polymer being synthetic or organic/natural, e.g., see Table 2) as well as other non-resorbable or non-polymeric materials (e.g., see Table 3); additionally, these materials may be used for a PEC region macrostructure, if one is employed. The macrostructure being a structure comprising voids, in which the PEC could be invested, along with other materials and therapies. In this type of embodiment, the materials and therapies are referred to collectively as the microstructure. The macrostructure and microstructure are also tailorable by other additions (e.g., see those materials and compounds listed in Tables 2 and 3).

In another embodiment, the void spaces within the macrostructure or microstructure, of any region, cause cellular regeneration effects by the size and/or shape thereof. That is, the relative size of the void space can affect the resulting cellular structure that is generated, or likewise the shape of the void space can affect cellular structure. Thus, engineering the size or shape of void spaces to stress or constrict cellular function can influence forms of regenerated tissue.

Similarly, the mechanical properties (e.g., density, hardness, modulus of elasticity, or compressive stiffness) or physical properties (e.g., macrostructure void, microstructure or a void therein, or cell attachment aiding material which is in the microstructure) of the host structure can alter the cellular reproduction type or phenotype. This is expected to be caused by the interaction between the host material and the endocellular fibrils, but other actions and reactions are anticipated to contribute to this effect. This interaction may be utilized to tailor the resulting cell type, by tailoring the host material's mechanical or physical properties.

TABLE 2

Examples and Sub-types of Bioresorbable Polymers for Construction of the Device Macrostructure and/or Microstructure of the Current Invention Aliphatic polyesters
Bioglass
Cellulose
Chitin
Collagen
    Types 1 to 20
    Native fibrous
    Soluble
    Reconstituted fibrous
    Recombinant derived
Copolymers of glycolide
Copolymers of lactide
Elastin
Fibrin
Glycolide/l-lactide copolymers (PGA/PLLA)
Glycolide/trimethylene carbonate copolymers (PGA/TMC)
Hydrogel
Lactide/tetramethylglycolide copolymers
Lactide/trimethylene carbonate copolymers
Lactide/ε-caprolactone copolymers
Lactide/σ-valerolactone copolymers
L-lactide/dl-lactide copolymers
Methyl methacrylate-N-vinyl pyrrolidone copolymers
Modified proteins
Nylon-2
PHBA/γ-hydroxyvalerate copolymers (PHBA/HVA)
PLA/polyethylene oxide copolymers
PLA-polyethylene oxide (PELA)
Poly (amino acids)
Poly (trimethylene carbonates)
Poly hydroxyalkanoate polymers (PHA)
Poly(alklyene oxalates)
Poly(butylene diglycolate)
Poly(hydroxy butyrate) (PHB)
Poly(n-vinyl pyrrolidone)
Poly(ortho esters)
Polyalkyl-2-cyanoacrylates
Polyanhydrides
Polycyanoacrylates
Polydepsipeptides
Polydihydropyrans
Poly-dl-lactide (PDLLA)
Polyesteramides
Polyesters of oxalic acid
Polyethylene Glycol
Polyethylene Oxide
Polyglycan Esters
Poly(Glycerol Sebacate)
Polyglycolide (PGA)

TABLE 2-continued

Examples and Sub-types of Bioresorbable Polymers for Construction of the Device Macrostructure and/or Microstructure of the Current Invention Polyiminocarbonates
Polylactides (PLA)
Poly-l-lactide (PLLA)
Polyorthoesters
Poly-p-dioxanone (PDO)
Polypeptides
Polyphosphazenes
Polysaccharides
Polyurethanes (PU)
Polyvinyl alcohol (PVA)
Poly-β-hydroxypropionate (PHPA)
Poly-β-hydroxybutyrate (PBA)
Poly-σ-valerolactone
Poly-β-alkanoic acids
Poly-β-malic acid (PMLA)
Poly-ε-caprolactone (PCL)
Pseudo-Poly(Amino Acids)
Starch
Trimethylene carbonate (TMC)
Tyrosine based polymers

TABLE 3

Examples of alternative materials that may be used for the macrostructure and/or microstructure of the current invention Alginate
Bone allograft or autograft
Bone Chips
Calcium
Calcium Phosphate
Calcium Sulfate
Ceramics
Chitosan
Cyanoacrylate
Collagen
Dacron
Demineralized bone
Elastin
Fibrin
Gelatin
Glass
Gold
Glycosaminoglycans
Hydrogels
Hydroxy apatite
Hydroxyethyl methacrylate
Hyaluronic Acid
Liposomes
Mesenchymal cells
Nitinol
Osteoblasts
Oxidized regenerated cellulose
Phosphate glasses
Polyethylene glycol
Polyester
Polysaccharides
Polyvinyl alcohol
Platelets, blood cells
Radiopacifiers
Salts
Silicone
Silk
Steel (e.g. Stainless Steel)
Synthetic polymers
Thrombin
Titanium
Tricalcium phosphate It is also contemplated that the PEC region, or the regeneration complex region, may be used alone (i.e., without a subchondral bone, or other region) or with a microstructure contained therein. Furthermore, it is recognized that when two or more regions are joined, as discussed in the various embodiments herein, there may exist a zone that is chemically or structurally distinct from either of, or one of, the regions. This may be incidental to the processing methods employed, or the natural reaction of the body's incorporation of the implant. That is, the zone may be intentional or a planned or unplanned result. For example, zones incorporating barriers and other active agents are within the scope of the invention. Furthermore, a zone incorporating a hydrophobic barrier wherein the surface properties of the macrostructure are altered (e.g., rendered hydrophobic) without altering the geometry or mechanical characteristics of the macrostructure is envisioned.

It is further contemplated that gene therapy may be used with PEC constructs, or similar devices for the regeneration of bone and soft tissue. Gene therapies are currently of two primary types, and are both together hereinafter referred to as "gene therapy" or "engineered cells". However, others are anticipated. The primary methodologies and basic understandings are described herein (see also Table 4).

First, nucleic acids may be used to alter the metabolic functioning of cells, without altering the cell's genome. This technique does not alter the genomic expressions, but rather the cellular metabolic function or rate of expression (e.g., protein synthesis).

Second, gene expression within the host cell may be altered by the delivery of signal transduction pathway molecules.

In a preferred embodiment, mesenchymal stem cells are harvested from the patient, and infected with vectors. Currently, preferred vectors include phages or viri (e.g., retrovirus or adenovirus). This preferred infection will result in a genetically engineered cell, which may be engineered to produce a growth factor (e.g., insulin like growth factor (IGF-1)) or a morphogen (e.g., bone morphogenic protein (BMP-7)), etc. (see also those listed in Table 4). Methods of infection as well as specific vectors are well known to those skilled in the art, and additional ones are anticipated. Following this procedure, the genetically engineered cells are loaded into the implant. Cytokines as described and used herein are considered to include growth factors.

Loading of the cells in this embodiment may be achieved prior to, during, or immediately following the implantation procedure. Loading may be achieved by various methods including, but not limited to, by injecting a solution containing the engineered cells into the implant, by combining the cells with the macrostructure, or by any void filling component, or by themselves, in the void spaces of any of the regions. Prior to the loading of fluid, whether by manual injection or by infiltration from the implant site, the PEC is referred to as being in a "dry state."

Other therapies, including but not limited to drugs, biologically active agents, and other agents, may also be utilized in or with the PEC, or any other associated or adjoined region (e.g., macrostructure or microstructure); either to aid the function of the PEC and/or any other associated or adjoined region or to cause other stimuli. The drugs, biologics, or other agents may be naturally derived or otherwise created (e.g. synthesized). For example, growth factors can be derived from a living being (e.g. autologous, bovine derived, etc.), produced synthetically, or made using recombinant techniques (e.g. rhBMP-2). Regardless of the time of investment or incorporation of these materials, they may be in solid particulate, solution gel or other deliverable form. Utilizing gel carriers may allow for the materials to be contained after wetting, for some tailorable length of time. Furthermore, additions may be incorporated into the macrostructure during manufacture or later. The incorporations may be made by blending or mixing the additive into the macrostructure or microstructure material, by injection into the gel or solid material, or by other methods known to those skilled in the art. Another method of incorporating additives, biologics and other therapies, into the macrostructure or microstructure of one or more regions of the device is through the use of microspheres.

The term "microsphere" is used herein to indicate a small additive that is about an order of magnitude smaller (as an approximate maximum relative size) than the implant. The term does not denote any particular shape. It is recognized that perfect spheres are not easily produced. The present invention contemplates elongated spheres and irregularly shaped bodies.

Microspheres can be made of a variety of materials such as polymers, silicone and metals. Biodegradable polymers are ideal for use in creating microspheres (e.g., see those listed in Tables 2 and 3). The release of agents from bioresorbable microparticles is dependent upon diffusion through the microsphere polymer, polymer degradation and the microsphere structure. Although most any biocompatible polymer could be adapted for this invention, the preferred material would exhibit in vivo degradation. It is well known that there can be different mechanisms involved in implant degradation like hydrolysis, enzyme mediated degradation, and bulk or surface erosion. These mechanisms can alone or combined influence the host response by determining the amount and character of the degradation product that is released from the implant. The most predominant mechanism of in vivo degradation of synthetic biomedical polymers like polyesters, polyamides and polyurethanes, is generally considered to be hydrolysis, resulting in ester bond scission and chain disruption. In the extracellular fluids of the living tissue, the accessibility of water to the hydrolysable chemical bonds makes hydrophilic polymers (i.e. polymers that take up significant amounts of water) susceptible to hydrolytic cleavage or bulk erosion. Several variables can influence the mechanism and kinetics of polymer degradation, including but not limited to material properties like crystallinity, molecular weight, additives, polymer surface morphology, and environmental conditions. As such, to the extent that each of these characteristics can be adjusted or modified, the performance of this invention can be altered.

In a homogeneous embodiment (i.e., monolithic or composite of uniform heterogeneity) of a therapy delivering implant material, the device provides continuous release of the therapy over all or some of the degradation period of the device. In an embodiment incorporating microspheres, the therapy is released at a preferential rate independent of the rate of degradation of the matrix resorption or degradation. In certain applications, it may also be necessary to provide a burst release or a delayed release of the active agent. The device may also be designed to deliver more than one agent at differing intervals and dosages. This time-staged delivery also allows for a dwell of non-delivery (i.e., a portion not containing any therapy), thereby allowing alternating delivery of non-compatible therapies. Delivery rates may be affected by the amount of therapeutic material, relative to the amount of resorbing structure, or the rate of the resorption of the structure.

Time-staged delivery may be accomplished via microspheres, in a number of different ways. The concentration of therapeutic agent may vary radially, that is, there may be areas with less agent, or there may be areas with no agent. Additionally, the agent could be varied radially, such that one therapy is delivered prior to a second therapy allowing the delivery of non-compatible agents, with the same type of sphere, during the same implant procedure. The spheres could also vary in composition. That is, some portion of the sphere population could contain one agent, while the balance may contain one or more alternate agents. These differing spheres may have different delivery rates. Finally, as in the preceding example, there could be different delivery rates, but the agent could be the same, thereby allowing a burst dose followed by a slower maintained dose.

In a time-phased delivery embodiment, the implant may be constructed to effect a tailored delivery of active ingredients. Both the presence of the implant and the delivery of the select agents are designed to lead to improvements in patients with tissue defects, as a result of delivering in no certain order: (1) a substratum onto which cells can proliferate, (2) a drug or biologically active agent which can act as a signaling molecule which can activate a proliferating or differentiating pathway, (3) a drug or biologically active agent which may act as a depot for nutrients for proliferating and growing cells, and (4) a drug or biologically active agent which will prevent an adverse tissue response to the implant, or provide a therapy which reduces infection and/or treats an underlying disease or condition.

In yet another embodiment, a matrix matched device is designed to mimic the properties of the host tissue and/or shape of any removed tissue, immediately upon implant or shortly after absorbing bodily fluids into the device's void network, or microstructure (if one is employed). The changing properties of certain polymers, following absorption or adsorption, of fluids is well known in the art. The device will afford a more natural feeling (than traditional implants), and minimize the feeling of a foreign body to the patient. As the device resorbs, it will foster the ingrowth or regeneration of tissue with properties matching or nearly approximating the host tissue, such that after a certain period of time (e.g., about two months to two years), the site of the procedure may have the pre-procedure look and feel restored. This embodiment may be especially beneficial for patients who have organs, tumors, or other tissue masses removed, and affords all of the therapeutic modes of the previous embodiments.

The device may matrix match the resulting tissue by preferentially altering the resulting scar tissue that is developed. Normal scar tissue occurs as fibrous bundles, with properties varying widely from the normal host tissue, and the structure of the implant device in this embodiment will tailor the growth of the scar tissue such that its properties will approach that of the native tissue. The structure of the implant is used to train the tissue, such that scar tissue forms in a non-bundled form (e.g., fibrous strands, more linear arrays, or smaller or thinner bundles), and the structure has enough integrity to support the growing tissue such that it does not contract non-uniformly, thereby avoiding or minimizing the disfiguring characteristics caused by shrinking of the tissues during final stages of growth and/or bundling. Additionally, this physical or geometric modeling of tissue may be aided by the delivery of a targeted therapy.

In the foregoing embodiments, it is envisioned that therapy delivery may be by way of incorporation of the therapy into the device matrix, macrostructure, microstructure, or microspheres (regardless of where located), and regardless of whether the therapy was delivered uniformly, time-staged, or as a burst dose. These methods of therapy delivery are localized in nature, as opposed to systemic approaches, that are necessarily delivered via the blood-stream. These systemic approaches concomitantly deliver therapies to various tissue and organs for which they were not intended. Localized delivery may allow higher doses, at the target site, than are tolerable to the body as delivered systemically. Chemotherapeutic treatment for certain cancers as well as other diseases may particularly be amenable to this type of therapy delivery, although various other procedures, not limited to those in Table 1, may benefit. Secondary therapies, or therapies delivered simultaneously with primary therapies, may be beneficial to reduce or eliminate side-effects of the primary therapy.

It is envisioned that time-staged delivery, whether achieved by a preferred placement of therapy within the macrostructure, microstructure, or microsphere, would allow staging of treatment, one of which stages may actually be detrimental to cell growth and proliferation, prior to the delivery of therapies that aid in tissue ingrowth or regeneration. Furthermore, tissue ingrowth and regeneration may have stages, such as, the initial nurturing therapy followed by rapid growth and proliferation aids.

As an example, Cisplatin and Paclitaxel are commonly used together in chemotherapeutic applications. These embodiments could deliver Paclitaxel at high dose rates initially, followed by lower dose rates of Cisplatin, which would occur over longer periods of time. It is also envisioned by this invention that the first therapy may be housed in a microstructural element (e.g., Paclitaxel) while the second therapy (e.g., Cisplatin) is housed in the matrix macrostructure. The slower resorbing macrostructure would supply the localized dose of the second therapy over the entire time during which any of the macrostructure remained.

In yet another embodiment, time-staged delivery or secondary therapy delivery may allow the function of tissue (e.g., organ such as the liver, etc.) to be replaced or supported, prior to, or concurrent with, regrowth or regeneration of diseased or removed tissue, or cellular transplant, which may be accomplished by the foregoing embodiments. This support may allow the tissue to slowly regain organic function, or reassume total function, whereas the otherwise diminished capacity may lead to total organ failure. Additionally, this support function therapy may be utilized to counteract a side effect of the primary therapy. As a non-limiting example, it may be used to support liver function during chemotherapy. The aforementioned localized delivery, together with secondary support, may allow the use of drugs not otherwise tolerated, or current drugs in greater dosages.

This type of cellular transplant embodiment may incorporate cells in any of the various regions, as disclosed in the other embodiments, or other sites within the implant (e.g., macrostructure, microstructure, void space, or microsphere). Additionally, therapies may be located in any of these regions.

TABLE 4

Examples with Some Sub-types of Biological, Pharmaceutical, and other Therapies Deliverable via the Device in Accordance with the Present Invention Adenovirus with or without genetic material
Alcohol
Amino Acids
    L-Arginine
Angiogenic agents
Angiotensin Converting Enzyme Inhibitors (ACE inhibitors)
Angiotensin II antagonists
Anti-angiogenic agents
Antiarrhythmics
    Amiodarone
    Lidocaine
    Sotalol
    Procainamide
    Diltiazem
Anti-bacterial agents
Antibiotics
    Erythromycin
    Penicillin TABLE 4-continued Examples with Some Sub-types of Biological, Pharmaceutical, and other Therapies Deliverable via the Device in Accordance with the Present Invention

- Imipenem
- Zosyn
- Cipro
- Flagyl
- Vancomycin
- Anti-coagulants
  - Heparin
  - Lovenox
- Anti-Fungals
- Anti-growth factors
- Anti-inflammatory agents
  - Dexamethasone
  - Prednisone
  - Aspirin
  - Hydrocortisone
- Antioxidants
- Anti-platelet agents
  - Forskolin
  - GP IIb-IIIa inhibitors
  - eptifibatide
- Anti-proliferation agents
  - Rho Kinase Inhibitors
  - (+)-trans-4-(1-aminoethyl)-1-(4-pyridylcarbamoyl) cyclohexane
- Anti-rejection agents
- Anti-restenosis agents
  - Adenosine $A_{2A}$ receptor agonists
  - Rapamycin
- Antisense
- Anti-thrombogenic agents
  - Argatroban
  - Fondaparinux
  - Hirudin
  - GP IIb/IIIa inhibitors
- Anti-TNF
- Anti-viral drugs
- Arteriogenesis agents
  - acidic fibroblast growth factor (aFGF)
  - angiogenin
  - angiotropin
  - basic fibroblast growth factor (bFGF)
  - Bone morphogenic proteins (BMP)
  - epidermal growth factor (EGF)
  - fibrin
  - granulocyte-macrophage colony stimulating factor (GM-CSF)
  - hepatocyte growth factor (HGF)
  - HIF-1
  - Indian hedgehog (Inh)
  - insulin growth factor-1 (IGF-1)
  - interleukin-8 (IL-8)
  - MAC-1
  - nicotinamide
  - platelet-derived endothelial cell growth factor (PD-ECGF)
  - platelet-derived growth factor (PDGF)
  - transforming growth factors alpha & beta (TGF-.alpha., TGF-beta.)
  - tumor necrosis factor alpha (TNF-.alpha.)
  - vascular endothelial growth factor (VEGF)
  - vascular permeability factor (VPF)
- Bacteria
- Beta blocker
- Blood clotting factor
- Bone morphogenic proteins (BMP)
- Calcium channel blockers
- Carcinogens
- Cells
  - Stem cells
  - Bone Marrow
  - Blood cells
  - Fat Cells
  - Muscle Cells
  - Umbilical cord cells
- Chemotherapeutic agents
  - 5-FU
  - Ceramide
  - Cisplatin
  - Cyclophosphamide
  - Doxorubicin
  - Flutamide
  - Imatinib
  - Levamisole
  - Methotrexate
  - Mitomycin
  - Oxaliplatin
  - Paclitaxel
  - Tamoxifen
  - Taxol
  - Topotecan
  - Vinblastine
- Cholesterol reducers
- Chondroitin
- Clopidegrel (e.g., plavix)
- Collagen Inhibitors
- Colony stimulating factors
- Coumadin
- Cytokines prostaglandins
- Dentin
- Etretinate
- Genetic material
- Glucosamine
- Glycosaminoglycans
- GP IIb/IIIa inhibitors
  - L-703, 081
- Granulocyte-macrophage colony stimulating factor (GM-CSF)
- Growth factor antagonists or inhibitors
- Growth factors
  - Autologous Growth Factors
  - Bovine derived cytokines
  - Cartilage Derived Growth Factor (CDGF)
  - Endothelial Cell Growth Factor (ECGF)
  - Epidermal growth factor (EGF)
  - Fibroblast Growth Factors (FGF)
  - Hepatocyte growth factor (HGF)
  - Insulin-like Growth Factors (e.g. IGF-I)
  - Nerve growth factor (NGF)
  - Platelet Derived Growth Factor (PDGF)
  - Recombinant NGF (rhNGF)
  - Tissue necrosis factor (TNF)
  - Tissue derived cytokines
  - Transforming growth factors alpha (TGF-alpha)
  - Transforming growth factors beta (TGF-beta)
  - Vascular Endothelial Growth Factor (VEGF)
  - Vascular permeability factor (VPF)
  - Acidic fibroblast growth factor (aFGF)
  - Basic fibroblast growth factor (bFGF)
  - Epidermal growth factor (EGF)
  - Hepatocyte growth factor (HGF)
  - Insulin growth factor-1 (IGF-1)
  - Platelet-derived endothelial cell growth factor (PD-ECGF)
  - Tumor necrosis factor alpha (TNF-.alpha.)
- Growth hormones
- Heparin sulfate proteoglycan
- HMC-CoA reductase inhibitors (statins)
- Hormones
  - Erythropoietin
- Immoxidal
- Immunosuppressant agents
- Immune modulator agents
- Inflammatory mediator
- Insulin
- Interleukins
- Interlukins
  - Interlukin-8 (IL-8)
- Lipid lowering agents
- Lipo-proteins
- Low-molecular weight heparin
- Lymphocites
- Lysine
- MAC-1

TABLE 4-continued

Examples with Some Sub-types of Biological, Pharmaceutical, and other Therapies Deliverable via the Device in Accordance with the Present Invention Methylation inhibitors
Morphogens
    Bone morphogenic proteins (BMPs)
Nitric oxide (NO)
Nucleotides
Peptides
Polyphenol
PR39
Proteins
Prostaglandins
Proteoglycans
    Perlecan
Radioactive materials
    Iodine - 125
    Iodine - 131
    Iridium - 192
    Palladium 103
Radio-pharmaceuticals
Secondary Messengers
    Ceramide
Signal Transduction Factors
Signaling Proteins
Somatomedins
Statins
Stem Cells
Steroids
Sulfonyl
Thrombin
Thrombin inhibitor
Thrombolytics
Ticlid
Tumor necrosis factor
Tyrosine kinase Inhibitors
    ST638
    AG-17
Vasodilator
    Histamine
    Forskolin
    Nitroglycerin
Vitamins
    E
    C
Yeast
Ziyphi fructus The inclusion of groups and subgroups in Table 4 is exemplary and for convenience only. The grouping does not indicate a preferred use or limitation on use of any drug therein. That is, the groupings are for reference only and not meant to be limiting in any way (e.g., it is recognized that the Taxol formulations are used for chemotherapeutic applications as well as for anti-restenotic coatings). Additionally, the table is not exhaustive, as many other drugs and drug groups are contemplated for use in the current embodiments. There are naturally occurring and synthesized forms of many therapies, both existing and under development, and the table is meant to include all forms.

Also within the inventive concept of the present invention is the placing of a plurality of microstructure materials at strategic locations within the same implant to perform multiple and varied biologic functions. For example, a large osteochondral defect may benefit from hyaluronan velour for microstructure in the subchondral region intended for osteoneogenesis. The placement of a different microstructure material can be accomplished by various methods, including investing the microstructure material into the regions before they are joined, by investing the device or regions thereof before joining from a first surface with a desired volume of microstructure material less than the total void volume of the macrostructure and then investing from the opposite surface with a volume of a different microstructure material equal to the balance of void volume of the macro structure.

Except for the critical location at the interface between the cartilage region (or first region, where applicable), the material of the subchondral bone region (or second region, where applicable) is hydrophilic by virtue of being treated with a wetting agent such as set forth in U.S. Pat. No. 4,186,448. For example, beginning at about 200 to 1500 micrometers, but more preferably 500 to 800 micrometers, from the interface surface and extending into the subchondral bone region, the macrostructure polymer of the subchondral bone region may be rendered hydrophobic, such as by treating the entire device or the subchondral bone region with a surfactant and then inactivating the surfactant in the hydrophobic barrier region (i.e., between its interface with the first and second regions or macrostructures), or by not treating the barrier surfaces with a surfactant while the remaining portions are treated.

Likewise, a hydrophobic barrier may be created within a device of simple (i.e. single) or complex (i.e. multiple) internal architectures by other means. For example, a separate fibrillar construct of bioresorbable polymer may be fabricated devoid of surfactant and may be interspersed between two segments of a device whose polymers have been rendered hydrophilic.

For example, in a simple device, such as one used to create cartilage and bone, the bone regeneration region (e.g., alpha-hydroxy-acid) is about 40 to about 90 percent of the apparent volume of the device, with the barrier located between the bone and cartilage regions. It is recognized that the barrier, as described above, may be a material distinct from the first and second regions, or it may exist at or near the surface of one of the regions, prior to the joining of the regions.

Furthermore, the barrier may, in a preferred embodiment, comprise interdigitations of the two joined regions.

In certain applications, it is envisioned that a total fluid or liquid barrier is a necessity, while other applications may have some tolerance or even a need for some liquid through-flow. The type and amount (quantity per application or number of applications) of surfactant can greatly influence the effectiveness of the barrier's inhibition of liquid flow interference. This invention contemplates a barrier that allows no fluid flow, as well as some small amount or retarded flow rate. This entire range of flow being referred to as "inhibited."

Additionally, the term surfactant, as used herein, envisions traditional ionic and stearic treatments, as well as dissimilar material coatings, utilized to alter the host material's response to water and/or certain other liquids. For example, it is envisioned that a hydrophilic coating may be applied to a hydrophobic structure or substrate, thereby rendering the body, or section thereof, hydrophilic, and vice versa.

Alternatively, other surface or chemical modification techniques may be utilized to create a suitable barrier between adjacent regions, or as an intraregional barrier. Such techniques include but are not limited to ion-beam activation, plasma, radio frequency, ultrasound, radiation, and thermal processing.

Water-based fluids, specifically fluid blood, brought to this locale by capillary action through hydrophilic polymer of the subchondral bone region closest to subchondral bone, are prohibited from traveling further toward the cartilage region by a hydrophobic polymer of the subchondral bone region in this vicinity. The interstices of the hydrophobic fibrillar membrane would eventually accommodate cell growth into, and/or migration through, the hydrophobic zone, but the immediate effect of such a membrane would be to prevent passage of water-based fluids across its boundaries.

The hydrophobic barrier is a significant advance and development for devices intended for use in chondroneogenesis, because hyaline cartilage, specifically the articular cartilage of joints, is an avascular tissue and should be protected from intimate contact with sources of high oxygen tension such as blood. When the recipient cartilage tissue defect is prepared to receive the implant, it is necessary to continue the defect into the underlying subchondral bone, called the cancellous bone, to assure that there will be new bone formed beneath the cartilage region which will produce a competent bond with the newly developing cartilage.

The customization of a microenvironment has been disclosed, wherein a three-dimensional architecture may support cell growth. However, the approach was that of a modified cellular structure, not a physical or geometric attribute (Grande, et. al.: A dual gene therapy approach to osteochondral defect repair using a bilayer implant containing BMP-7 and IGF-1 transduced periosteal cells. 47$^{th}$ Annual Meeting, Orthopaedic Research Society, Feb. 25-28, 2001, San Francisco, Calif.). This technique differs from the present invention as it does not include any subchondral bone sector. Therefore, complete natural bonding between bone and cartilage of sufficient integrity remains problematic.

A similar technique has recently been disclosed, which includes a partition of the microenvironments (Gao J, et. al.: Tissue engineered osteochondral graft using rat marrow-derived mesenchymal stem cells. 47$^{th}$ Annual Meeting, Orthopaedic Research Society, Feb. 25-28, 2001, San Francisco, Calif.). That construct has two regions glued together with fibrin glue. The regions comprise insoluble hyaluronic acid and tricalcium phosphate. The drawback of this construct is that the barrier is hydrophilic. Additionally, the fibrin glue is quickly bioresorbable and lacks significant adhesive strength. Further, hydrophilic barriers of this construct allow the transport of body fluids and soluble cytokines between regions, which interrupts chondrogenesis and osteogenesis. Barriers which are quickly bioresorbable promote unstable interfaces resulting in mechanical and biological insufficiencies.

Tissue preparation, such as this, engages the rich collateral circulation of subchondral cancellous bone and its associated bone marrow. If the cultured chondrocytes or host cartilage cells come into contact with the fluid blood produced by this source of collateral circulation, they will fail to maintain their chondrocyte phenotype. However, the hydrophobic barrier as may be employed in the present invention described above isolates the cartilage region from contact with whole blood originating in the subchondral bone region. This tissue-specific construct is exemplary, as other regions or tissues and other fluids are contemplated.

It can be appreciated that an anatomically specific device, which may be bioresorbable, according to the teachings of the foregoing inventions having a fabricated macrostructure closely resembling the mature tissues which are to be regenerated by the completed implant, has particular value. Further, integrating one or more of a macrostructure, microstructure, cells cultured in vitro, culture medium and associated growth factors, morphogens, drugs and other therapeutic agents may additionally be beneficial.

According to the teachings of the present invention, the device can be utilized as a transport system for chondrocytes, growth factors, morphogens and other biologically active agents, in treatment of articular cartilage defects. Suitable source tissue is harvested, and the cells are cultured using standard chondrocyte culturing methods, with the specific cell type in the preferred form being articular cartilage chondrocyte. The cartilage defect is surgically prepared by removing diseased or damaged cartilage to create a cartilage and subchondral bone defect, with the defect extending approximately 0.5 cm to 1.0 cm into subchondral cancellous bone. With the device and defect having generally the same shape, the device is inserted into the tissue defect such as by press fitting. A volume of in vitro cell culture suspension is measured out by a microliter syringe which generally matches exactly the void volume of the cartilage region macrostructure invested by the microstructure and is injected onto the outer surface of the tangential zone of the cartilage region and which will ultimately be in contact with synovial fluid. The joint anatomy can then be replaced in proper position and the wound can be closed.

Alternatively, cells or other therapeutic additives may be incorporated during the manufacture of the device, or during the final device preparation (i.e., immediately prior to implant), or as briefly noted above following the implant procedure (e.g., prior to wound closure or as a later therapy, following wound closure).

Although the preferred form relates to the transport and/or in vivo culturing of chondrocytes, it should be noted that the teachings of the present invention, and the useful devices fabricated as a result thereof, are intended to culture and/or transport, and to sustain in life, any cell type having therapeutic value to animals and plants. Various other cell types would be beneficial for tissue other than cartilage or bone, depending on the site and application. The various uses outlined above, in text and tabular form, are contemplated by this invention.

The term "therapy" has been used in this specification, in various instances. Notwithstanding these various uses, many in combination with other agents (e.g., drug, biologic, biologically active agents, etc.), therapy is not meant to be exclusive of these, but rather to incorporate them. The usage herein is employed to be more descriptive of potential treatment forms, and not limiting as to the definition of the term.

Recall that a second major aspect of the invention focuses on the delivery of one or more therapeutic agents from the device. Referring now in greater detail to the various embodiments depicted by the figures of the drawings of the device of this aspect of the present invention, wherein like reference characters refer to like parts, there is shown in FIG. 1 a construct 10 for delivering a therapeutic agent to a tissue. The construct 10 depicted has an outer surface 14 and a porous body 16. The body of the construct is designed to deliver therapeutic agents to adjacent and/or nearby tissue over a length of time. The construct may incorporate one or more designs to deliver the agents. Although shown to be porous, the body of the construct 16 may be non-porous or substantially non-porous. Additionally the material of the body of the construct may be resorbable, non-resorbable or a combination of resorbable and non-resorbable materials. In a preferred embodiment, the outer surface 14 may be on the opposite side of the construct from the targeted tissue. In another embodiment, the outer surface 14 may be arranged to deliver a second therapy (different from the therapy delivered by the body 16) either locally or systemically. The second therapy may serve to counter an effect of the first therapy in non-target tissue, in which case, the second therapy would likely be delivered systemically. In another preferred embodiment, the outer surface 14 may be an indistinguishable continuation of the body 16 of the construct 10. The porous body may comprise a macrostructure and microstructure, similar to that described above, or alternatively, may comprise a macrostructure without a microstructure.

A representative, but not exhaustive, list of resorbable materials used for the manufacture of the porous body, and any macrostructure or microstructure, is shown in Table 2.

Figure 2:
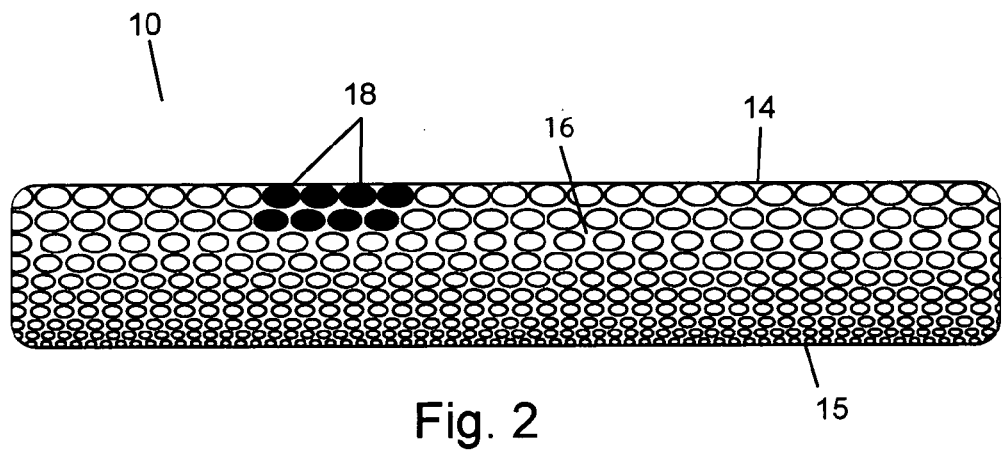
FIG. 2 is an enlarged sectional view of an embodiment of the construct.

FIG. 2 is an enlarged sectional view of the construct 10 demonstrating the outer surface of the construct 14, the drug delivery surface 15 and the body of the construct 16. In a preferred embodiment the outer surface of the construct 14 is non-permeable to liquids or the therapeutic agents contained within the construct. As a result, the therapeutic agent exits the construct through the drug delivery surface, which is in contact with the targeted tissue and not into the nearby surroundings through the outer surface 14. In another preferred embodiment, there may be no effective outer impermeable surface, as the therapeutic agent may be released from all sides or surfaces of the construct 10. Alternatively, at least a portion of the targeted tissue may not be in contact with the drug delivery surface, for example, the drug delivery surface may contact directly a small portion of an organ, such as the atria, however, a larger portion of the target tissue (e.g., the entire organ) may be subjected to the locally delivered drug or therapy, such as through diffusion, preferably without systemic effect. A porous embodiment of the construct is shown in FIG. 2 with material depicted within the pores 18. Referring to a porous embodiment of the construct, the therapeutic agent may be incorporated into the material making up the body of the construct (e.g., directly into a macrostructure), within the pores of the construct (e.g. as, or contained within, the microstructure incorporated into the voids of the macrostructure), attached to or within an additional material (e.g. particulates, granules, microspheres, gel, solid material, freeze dried material, etc.) inserted into the pores of the construct or any combination of the above. A material such as hyaluronic acid may be added to the therapeutic agent within the pores to alter its release from the pores and subsequent delivery to the adjacent tissue. In another preferred embodiment, the pores 18 may be filled with a liquid, gel, or solution containing one or more therapeutic agents. Furthermore, the construct 14 may completely or partially comprise a gel.

In a preferred embodiment, the combination of therapeutic agents incorporated within the body material 16 (e.g. macrostructure) of the construct 10 and within the pores 18 allows for complex and precise delivery of one or more therapeutic agents to the tissue. For example, the material of the body of the construct may be a 50%/50% PGA/PLA polymer with dexamethasone incorporated into the polymer and the pores of the polymer filled with a dexamathasone-hylauronic acid suspension and microspheres of 20%/80% polycaprolactone/PLA polymer with incorporated dexamethasone. This would result in a complex but well orchestrated delivery of the therapeutic agent dexamethasone to the tissue as the dexamethasone-hyaluronic acid would first resorb and begin to release the dexamethasone into the tissue within minutes to hours of application. A relatively quickly resorbing polymer, such as the 50%/50% PGA/PLA polymer provided in this preferred embodiment would then release dexamethasone into the tissues over days to months, and finally a slower resorbing material, such as the polycaprolactone-PLA polymer microspheres would resorb last, but in slowly resorbing would maintain a low, but sufficient, release of dexamethasone.

The pores 18 within the construct 10 may be uniform in size or shape throughout the thickness of the construct, or alternatively, may vary in either size or shape. A variation in pore size may in part control the release of therapeutic agents into the tissue. Similarly, variations in pore shape may serve to control the release of an agent. This may occur as folds or invaginations in pore shape serve to maintain or prevent the entrainment of materials, such as microspheres or particulates, within the pores after body fluids have entered the pore cavity. As an example of controlling drug delivery characteristics of the construct through pore size variation, a construct having large pores at the delivery surface 15 (the surface adjacent the targeted tissue) and smaller pores near the outer surface 14 away from the targeted tissue, may have a quicker or larger release of therapeutic agent from the pores initially. Conversely, as depicted in FIG. 2, a construct having pores which are smaller at the delivery surface 15 and larger near the outer surface 14 may have a higher steady state release over time and less of an initial release.

It is recognized that the pores within a construct of the present invention may be as small as about 2 microns or less, thereby providing some benefit, such as the prevention of cellular infiltration or providing slow drug release. Further, the pores within the construct may be relatively large, such as about 5 mm, and may serve to provide pockets for rapid drug dissolution. Preferably, the pores are about 10 microns to 2000 microns, more preferably, pores are sized from 100 microns to 500 microns.

Primarily the combination of materials, pore size, construct thickness and initial water content determines the response of the construct after it is contacted with water or a solution. The construct may be manufactured such that upon contact with water or a solution, the construct 10 shrinks or contracts. This response of the construct may aid in its adhesion to tissue. For example, the construct in a dry state is placed on the atrium of the heart and the construct is gently hydrated with a saline irrigation. The construct may slightly shrink and adhere to the atrium by conforming to the non-planar shape of the surface of the atrium. This may allow the construct to remain in place without the use of any secondary attachment means. Alternatively, the construct may use secondary attachment technologies to ensure that it remains in approximation to the desired tissue and it has non-obstructed contact with the tissue. Attachment technologies which may be used include those known in the art (e.g., suturing the construct to the tissue, adhesives, UV activated adhesives, staples, nitinol wire, clips, magnets, static bonds, physically interlocking components, salts, carbohydrates, gelatins, hydrogels, etc.). It is recognized that an attachment technology may be utilized alone, or in combination with other attachment technologies in order to achieve a more effective placement of the construct.

In another embodiment of the construct, the shape of the construct may be manufactured or modified prior to placement in a manner such that the construct contacts the precise tissues necessary to adequately deliver the therapeutic agent for maximal effect. For example, in the application where the construct is delivering therapeutic agents to the atrium, the shape of the construct may be modified prior to placement such that the construct contacts both the atrium and the pulmonary veins. Additionally one or more constructs may be used in any application to ensure adequate tissue contact to optimize delivery of therapeutic agents.

Furthermore, the construct may be applied to a small area if that is all that is needed for the therapeutic agent to have the desired effect on the tissue. For example, the construct could be delivered to a portion of the atrium and deliver a therapeutic agent. If this portion of the atrium was within the pericardial reflection, the construct may be delivered through a minimally invasive technique by accessing the pericardium and placing the construct on the appropriate portion of the atrium or other heart structure using techniques known in the art, such as catheter, robotic, laproscopic, fluoroscopic or other known minimally invasive techniques.

Figure 3:
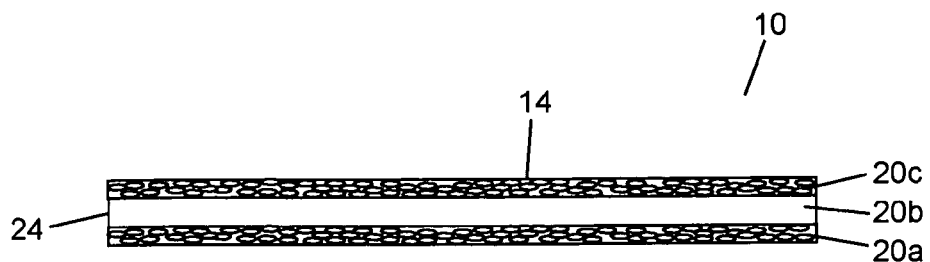
FIG. 3 is an enlarged sectional view of an embodiment of the construct.

Another preferred embodiment of the construct 10 is shown in FIG. 3. The outer surface 14 of the construct may be porous in continuity with the body of the construct or may have a different porosity including being non-porous. A non-porous outer surface (e.g. impermeable membrane or cover) 14 may prevent the release of a therapeutic agent from the construct 10 into tissue contacting the outer surface 14 which may not be the targeted tissue for delivery of the therapeutic agent. Alternatively, if the construct is placed adjacent tissue where delivery of therapeutic agent from one ore more sides of the construct is desired, the porosity, materials, concentration of therapeutic agent and other controlling factors may be adjusted to ensure the desired delivery of therapeutic agent to the tissues. Additionally, in the embodiment shown in FIG. 3 where the construct 10 has a generally rectangular cross-section the sides 24 of the construct may also be porous or non-porous according to the desired release of therapeutic agent. If the shape of the construct 10 needs to be changed prior to placement on or near a tissue to ensure optimum size for tissue contact, the construct may be modified, for example cut, compressed, stretched, or connected to another construct in a manner which gives it the optimum shape prior to or after contact with the tissue. Modification of the construct may be done with sharp division, heat, electrical current, laser, compression or other means or combination of means to effect the desired edge of the construct after modification. For example, sharp division of a porous construct may result in a porous edge for release of therapeutic agent from the pores through said edge whereas compression and division with heat may result in a sealed or non-porous edge for prevention of release of therapeutic agents. In another preferred embodiment, the construct may be spherical, rectangular, planar, curved, or any other common or custom shape necessary to optimally contact tissues and deliver therapeutic agent.

In FIG. 3, a multilayered construct 10 is shown. Construct layers 20a, 20b, and 20c are shown where layers 20a and 20c are porous containing therapeutic agent in their structure and within the pores, and layer 20b is substantially non-porous containing therapeutic agent only within its structure. The combination of porous and non-porous layers, multiple therapeutic agents, material composition, thickness and processing allows endless multitude of elution profiles for multiple therapeutic agents. In addition to delivery of a therapeutic agent(s), an additional agent may be delivered. Among other functions, the additional agent may serve to reduce the absorption of the therapeutic agent by blood vessels within the targeted tissue. For example, an additional agent may vasoconstrict the vessels of the atria in order to limit systemic absorption of the therapeutic agent. This may allow significant doses of anti-inflammatory, immunosuppressive, immunomodulating or other therapeutic agents to be used with minimal systemic effects. A representative list of therapeutic agents is included in Table 4.

The layers 20a, 20b, and 20c of FIG. 3, may have additional functions, such as contributing to the adhesive component of the construct. The layer closest to the target tissue 20a may be initially attached or detached from the construct. It may have as its sole or partial purpose to providing for adhesion of the construct to the tissue, whether through contraction, adhesives or other methods as previously described. Further, it may provide a surface which subsequent layers 20b can easily adhere or be joined. In the event that layer 20a is applied to the target tissue first for primarily adhesive purposes, it may preferably have porosity equal to or greater than that of the other layers.

The construct 10 may have additional functions such as the prevention of adhesions of tissue to the construct or the prevention of adhesions between tissues separated by the construct. The portion of the construct 10 furthest from the target tissue may have the sole or additional function of preventing adhesions. The material(s) used in this layer may be the means of adhesion prevention, alternatively therapeutic agents could be released from the construct 10, the outer surface 14 or the outer layer 20c to prevent adhesion formation. In another embodiment the construct 10 could incorporate additional layers that prevent the formation of adhesions. The anti-adhesion technology described in U.S. patent application Ser. No. 10/850,631 which is incorporated herein by reference, could be used with this described construct to prevent adhesions from occurring. In an alternative embodiment, this construct 10 could be used to prevent adhesions between a tissue structure such as the chest wall or sternum (or other tissues beneath or near the surgical incision as the incision may not be a median sternotomy) and the heart (or other tissue adjacent to or near the surgical incision) in addition to delivering therapeutic agents to prevent post-operative atrial fibrillation.

Therapeutic agents delivered by the construct may be designed to impact the intended tissue and reverse or prevent a disease process and they may also be used to prevent or minimize a reaction the presence of the construct itself. Antibiotics, anti-inflammatory and other therapeutic agents may be used to minimize any foreign body reaction to the construct and prevent any unwanted impedance of delivery of therapeutic agents.

Figure 4:
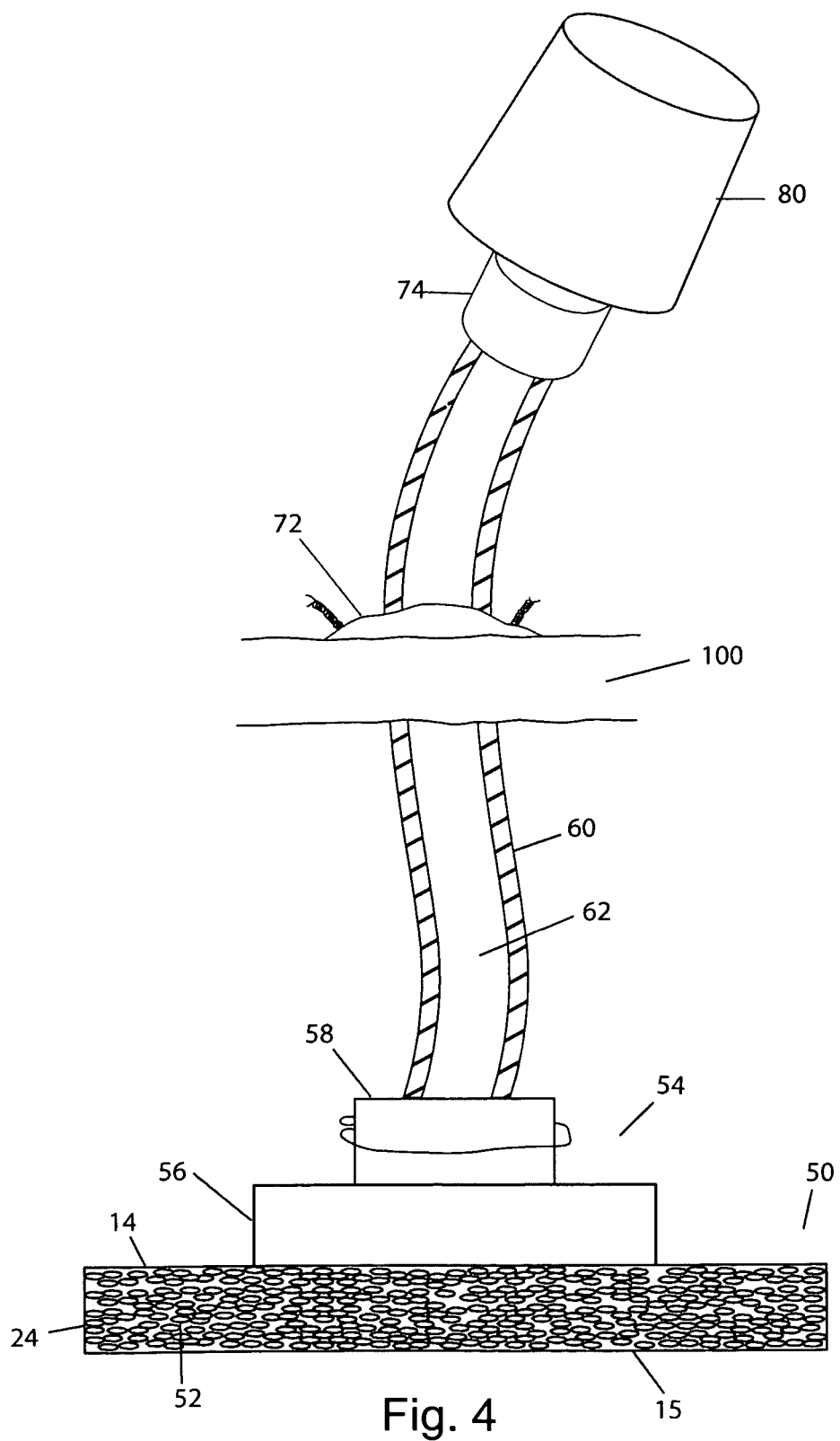
FIG. 4 is an isometric view of an embodiment of the construct.

In another preferred embodiment, FIG. 4 demonstrates a construct 50 with outer surface 14, side surface 24, agent delivery surface 15 and body 52. Attached to or contiguous with the outer surface is an infusing connector 54 with base 56 and connecting port 58. This construct 50 utilizes, partially or completely, an external source 80 for supply of a therapeutic agent for delivery to the tissue. The body 52 of the construct 50 has a sufficiently open porous structure to allow the dispersion of a therapeutic agent delivered through the infusing connector to the agent delivery surface 15 of the construct adjacent to tissue. The body 52 of the construct may be an open porous structure that facilitates dispersion of the therapeutic agent across the entire construct 50 so there is delivery of the agent to the targeted tissue adjacent to the entire agent delivery surface 15. The portion of the body near the outer surface 14 may have a different porosity or different degree of communication between adjacent pores than the portion of the body near the agent delivery surface 15. For example, a open porosity with significant communication between pores near the outer surface 14 will allow uniform dispersion of the agent, especially if the solution containing the therapeutic agent is water based. The pore sizes near the agent delivery surface 15 may have to be smaller and communicate with the larger open pores near the outer surface 14 and not with adjacent pores in the plane of the delivery surface. This would allow delivery of more therapeutic agent to a particular portion of the targeted tissue by making the relative pore size at the agent delivery surface 15 larger for more agent delivery and smaller for less agent delivery. The presence of an open porous structure near the outer surface of the construct 14 is an improvement over the prior art, as the construct may be placed on a non-planar targeted tissue with a variable position relative to gravity as the patient moves. A simple open space near the outer surface 14 of the construct may result in pooling of the therapeutic agent in the gravity dependent portion of the construct if a liquid phase therapeutic agent is utilized. This would result in non-uniform or non-controlled delivery of the therapeutic agent to the targeted tissue. A construct with an open porous structure near the outer surface 14 where the therapeutic agent enters the construct via the delivery tube 60 and the base 56 and connecting port 58, the capillary action of a liquid phase therapeutic agent will draw the therapeutic agent through the construct and result in at least relatively uniform dispersion of the agent to the targeted tissue. The viscosity, delivery pressure, and desired flow rates of the therapeutic agent will need to be matched with the pore size and degree of communication to achieve optimum distribution across the construct.

The delivery tube 60 with lumen 62 passes through the skin and body wall 100 to join the construct at the connecting port 58. Outside the body, a connector 74 joins the delivery tube 60 with an external supply of therapeutic agent 80. An external connector 72 provides securement and aids in maintaining the sterility of the delivery tube 60 as it enters the body wall 100. The delivery tube 60 is releasably attached to the connecting port 58 to be described in more detail in FIG. 5. In a preferred embodiment, the delivery tube 60 may be removed from the body, leaving the construct 50 with infusing connector 54 in place in the body. In this configuration, the construct 50 with infusing connector 54 may be constructed of resorbable materials while the delivery tube 60 may be constructed with non-resorbable materials (such as silicone or polyurethane). The construct 50 may be placed in the body and with use of the delivery tube 60 therapeutic agent(s) may delivered to the target tissue for a finite period of time. With this embodiment or other embodiments of the present invention, the tissue response to the therapeutic agents could be monitored and the dosage altered (either by varying the quantity and/or rates of therapy delivered, or the choice of therapeutic agent components being delivered) when deemed medically appropriate. Additionally, when delivery of therapeutic agents are no longer required the non-resorbable delivery tube may be removed in the office or at the bedside without need for a surgical procedure and the construct 50 with infusing connector 54 would be resorbed over time. This construct would allow for infinite flexibility in the timing and dosage of therapeutic agent(s) and would allow for monitoring of the tissue response to the therapeutic agents through imaging, blood tests, clinical exam and other means and subsequent adjustment or termination of the delivery of therapeutic agents.

In one example, the embodiment of FIG. 4 may be used to delivery an anti-inflammatory regimen of therapeutic agents to the atrium, pulmonary vein, vena cava and ventricles following heart surgery. In the event that the patient develops atrial fibrillation despite initial treatment, the delivery of anti-inflammatory drugs with possibly a different regimen or the addition of other classes of drugs, for example an antiarrythmic such as amiodarone could be added. A change in treatment after monitoring the patient's initial response to the therapeutic agent may terminate the arrhythmia quickly and obviate any additional treatments and avoid any associated morbidity.

Such a construct could be used to deliver therapeutic agent to prevent post-operative atrial fibrillation as described above and could also be used in a litany of other medical applications. Local delivery of chemotherapeutic agents is another anticipated use for the construct described here. Used as sole or adjunctive treatment, delivery of a chemotherapeutic agent using an independent delivery construct as described in FIG. 1 or a complex system of delivery with an external source as described in FIG. 4 could greatly improve the treatment of benign and malignant proliferative diseases. For example, a construct could be placed in the surgical bed following a resection for breast cancer to deliver adjunctive chemotherapy. Similarly the construct could be placed against the parietal pleura over a mesothelioma to deliver high dose chemotherapy. Placement of the construct through minimally invasive means may deliver beneficial treatment for adjunctive treatment. For example, laproscopic placement of the construct in the abdomen adjacent to a peripheral liver tumor, gastric tumor, pancreatic tumor, ovarian tumor or other benign or malignant process may provide beneficial pre-surgical or sole chemotherapeutic treatment. Placement of the construct in a post-resection treatment bed may be curative or may significantly reduce any residual tumor burden especially in node positive, margin positive or cases with known metastatic disease.

In another example, the embodiment of FIG. 4 may be used to deliver radiation to a tissue. In the event that the construct is positioned to treat a cancer, the delivery tube and construct may be used to deliver radioactive isotopes in microspheres adjacent to the tissue. This particular strategy may be quite useful when the decision to use radiation is based on response to chemotherapy (possibly delivered with the same construct) or outcome of pathology following surgery when a construct is placed intraoperatively. Additionally it may be used to deliver radiation as a substitute for daily radiation treatments. Additionally, the presence of molecular oxygen is important in the mediation of the indirect effects of radiation on cells. The effect of free radicals generated by the interaction of the radiation and the water within the cells is enhanced in the presence of molecular oxygen. In this invention, oxygen in the form of a gas could be delivered to the tissue via one or more of the constructs presented in addition to or without the local delivery of radiation. Namely oxygen could be delivered to the tissue by itself, with locally delivered radiation via the construct or with externally delivered radiation. This presence of additional molecular oxygen at the site of the targeted tissue could greatly enhance the effect of the radiation. In another preferred embodiment, the construct may be used to deliver a molecule or agent which can be broken down into molecular oxygen or another molecule or construct which may increase or otherwise therapeutically modify the effect of radiotherapy (for example hydrogen peroxide which can be broken down into oxygen by an enzyme present in the body. The construct could also be used to deliver pharmacologic modifiers to increase the effectiveness of the radiotherapy, for example, halogenated pyrimidines (bromodeoxyuridine, idoxuridine, etc.) and chemotherapeutic drugs such as hydroxyurea. The construct may be utilized to deliver a first therapy (e.g., a radiopharmaceutical) locally to specific tissue (e.g., cancerous tissue) from a first surface, material or portion of the construct, and additionally (whether concurrent with or not) may deliver a second therapy (e.g., radiation mediators) from a second surface, material or portion of the construct systemically to non-specific tissue.

The physiologic effect of sustained magnetic fields on tissue is unclear but the construct could be used to deliver magnets or magnetic fields to targeted tissue for a therapeutic benefit.

Figure 5:
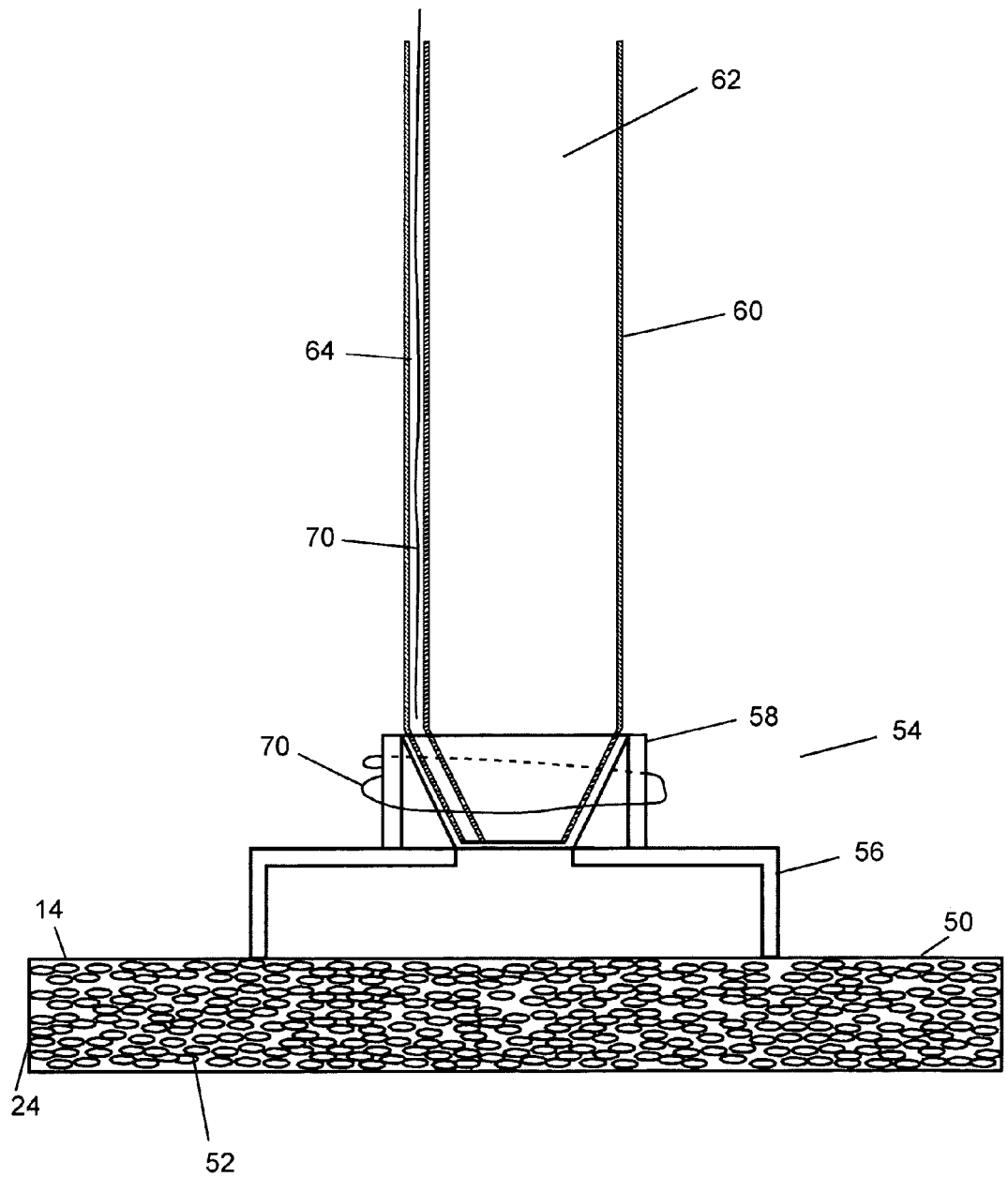
FIG. 5 is an enlarged isometric view of a portion of an embodiment of the construct.

FIG. 5 demonstrates the releasable connection between the delivery tube 60 and the infusing connector 54 with base 56 and connector port 58. The delivery tube 60 has a delivery lumen 62 for the infusion of a therapeutic agent and a filament lumen 64 where a filament 70 extends within the delivery tube and exits to secure the delivery tube to the connector port 58 of the infusing connector 54. There are multiple arrangements of the filament to secure the delivery tube to the connector port with only one shown here where the filament 70 circumvents the outer portion of the connector port 58 (the connector port may have a groove, not shown, which the filament lies in) and reenters the delivery tube 60 and into the filament lumen 64. Both ends of the filament may extend out of the body to or near the connector 74 (with reference to FIG. 4), alternatively one filament may be secured to the delivery tube 60 near the distal end where it connects to the construct 50. The design may allow for release or division of one or both ends of the filament to permit the delivery tube 60 to be autramatically removed from the connector port 58 without causing separation of the construct 50 from adjacent tissue. The delivery tube 60 could then be removed from the body without a separate surgical operation. As previously described, if the construct was made of resorbable materials it may remain in the body and be resorbed without adverse effects. In another preferred embodiment, the construct may be formed of a non-resorbable material which would maintain its structure longer than a resorbable material and once therapy is completed, the delivery tube is removed and the construct remains in the body. Accordingly, the construct may be constructed of adequately biocompatible material as to not elicit an adverse response. The construct 50 and the infusing connector 54 may be made of different materials to ensure the optimum performance and function of each component. The infusing connector 54 and specifically the connector port 58 may have multiple seals with the delivery tube 60. As an example, one type of seal may be a tapered fit between the delivery tube 60 and the connector port 58 which is secured by the filament 70 as shown in FIG. 5.

Figure 6:
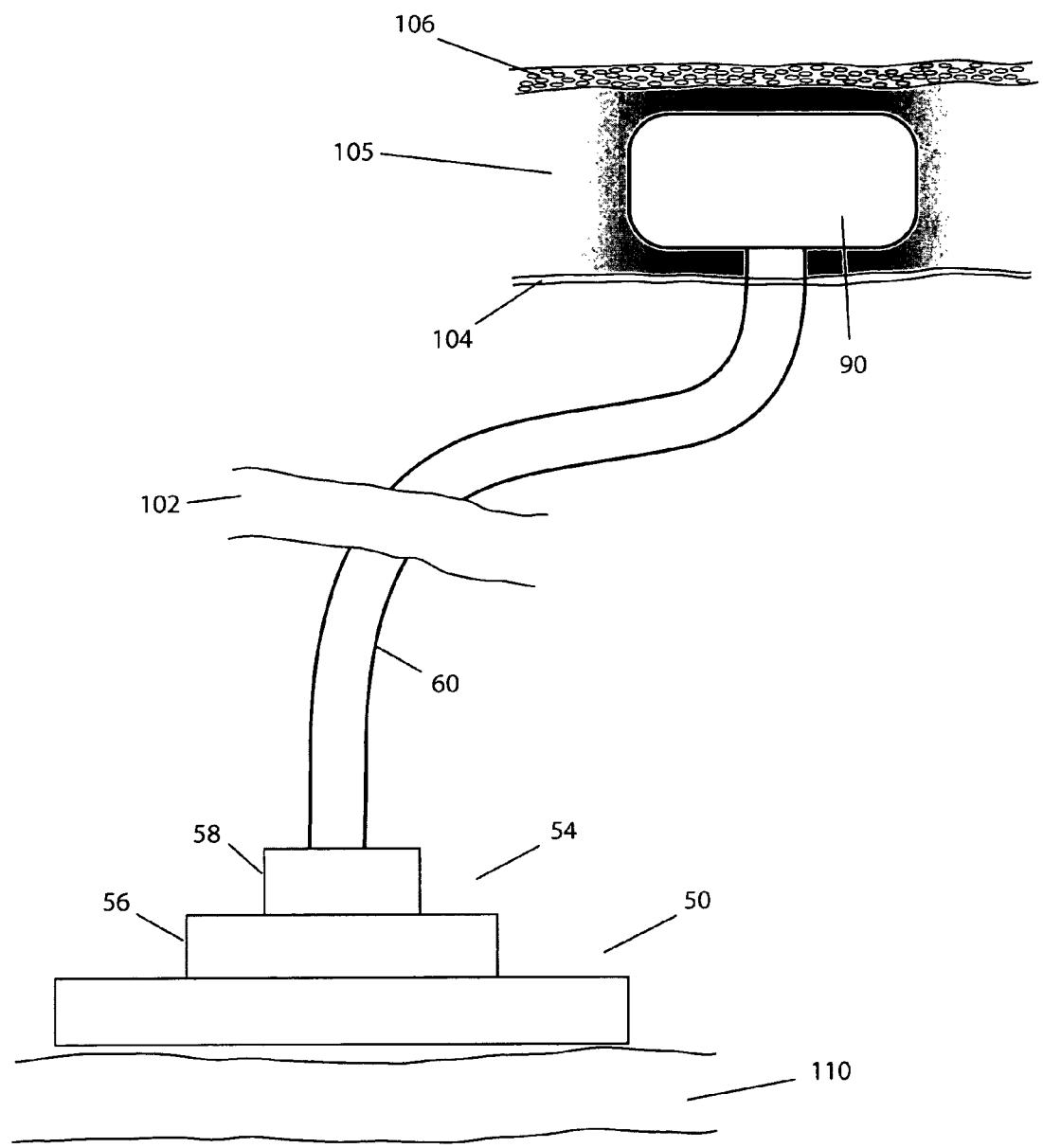
FIG. 6 is an isometric view of an embodiment of the construct.

Another preferred embodiment is shown in FIG. 6 where the construct 50 is positioned adjacent the targeted tissue 110 and the delivery tube 60 extends from the construct 50 through a tissue structure 102 and terminates at a port 90 beneath the skin 106. This embodiment represents another configuration of the placement of the construct 50 and the utilization of a port 90 to deliver a therapeutic agent to a targeted tissue 110. The port 90 may lie in the subcutaneous tissue 105 between the skin 106 and the fascia 104. The delivery tube may pass through an intermediate tissue structure 102 such as the diaphragm en route to an acceptable site within the subcutaneous tissues 105 or through the skin 106 as previously described. The port 90 beneath the skin improves the sterility of the construct 50 and delivery tube 60 in the event that the device needs to be in place for an extended period of time. The port 90 may function simply as a method of repeatedly delivering therapeutic agents or it may have a more complex mechanism. For example, the port may have a mechanism that maintains the pressure or flow of delivery of the therapeutic agent into the tissue fixed at a particular level. The port construct 90 may also be a reservoir that contains enough of a therapeutic agent for a prolonged period of time. The port may be computer controlled and may be adjustable via wired or wireless control. The port may have multiple reservoirs for the simultaneous or staged delivery of multiple therapeutic agents. The agent(s) may be delivered to the tissues in pulsatile manner.

Figure 7A:
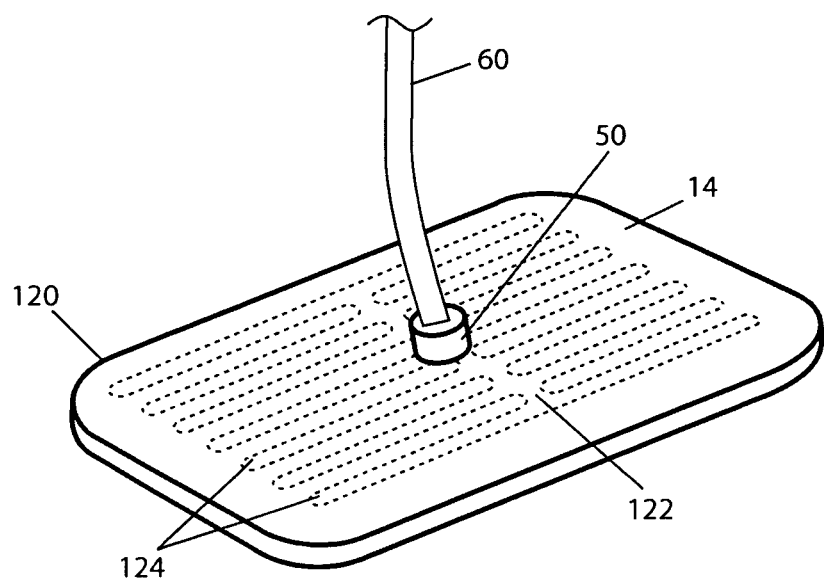
FIG. 7A is an isometric view of an embodiment of the construct.
Figure 7B:
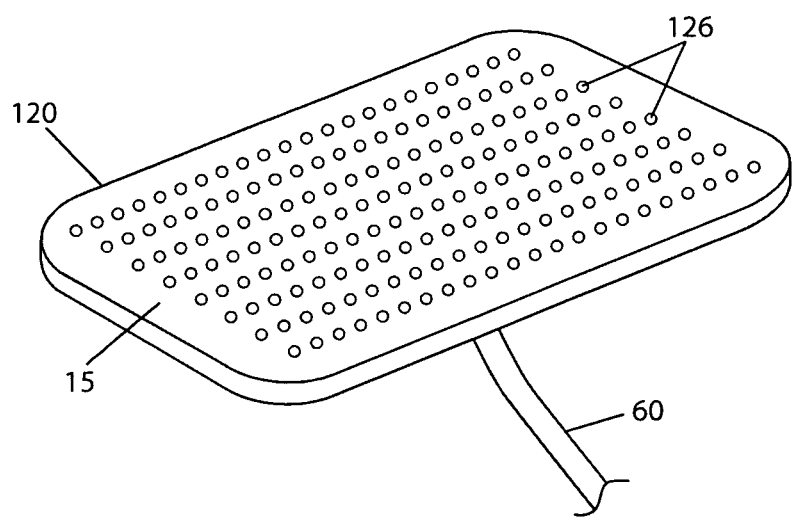
FIG. 7B is an isometric view of an embodiment of the construct.

Another preferred embodiment is shown in FIG. 7A wherein the construct 120 has an outer surface 14, a delivery tube 60 and a connector port 58. The delivery tube 60 is in communication with a primary space 122 within the construct 120. The primary space 122 serves to distribute the therapeutic or diagnostic agent within the construct 120 for eventual delivery to the targeted tissue. The primary space 122 may be in communication with secondary spaces 124 that may further deliver the contents of the delivery tube 60 within the construct 120. The shape of the primary 122 and secondary 124 spaces shown in FIG. 7a are exemplary only. It is recognized the shapes may vary, and be in various forms, such as an open space, a complex network of channels, and the like, wherein the desired goal of distributing the therapeutic agent within the construct is achieved. Referring to FIG. 7B, the construct 120 has an agent delivery surface 15 which may incorporate one or more openings 126 for the delivery of a therapeutic agent. The openings 126 may be in communication with the primary 122 and secondary 124 spaces described in FIG. 7A. The arrangement of the openings 126 may be in a manner such that optimal delivery of a therapeutic agent is achieved. Furthermore, the openings may be of the same or varied diameter such that the flow through the openings is in part controlled by the size of the opening. This feature may allow the selective delivery of more therapeutic agent through a portion of the agent delivery surface 15 and may also aid in the regulation of the rate of therapeutic agent delivery. The delivery tube 60 may be attached to a therapeutic agent delivery source as previously described. The delivery source may use constant pressure as a means of delivering the therapeutic agent. In that case, the size of the openings 126 (individually and collectively) could be a determining factor regulating the flow rate of the therapeutic agent. If a therapeutic agent delivery source uses a constant flow, the size of the openings would serve to determine the maximum allowable flow given the viscosity of the therapeutic agent as well as the distribution of the agent across the agent delivery surface 15 as the larger holes would be capable of delivering more agent than the smaller holes. Alternatively, uniformly sized holes would result in a uniform delivery of therapeutic agent to the tissue.

In the treatment or prevention of atrial fibrillation, the construct may be applied during surgery on the heart or it may be applied to the heart during an isolated procedure. If the construct is applied during an open chest or laparoscopic chest procedure to prevent postoperative atrial fibrillation, multiple constructs may be used to achieve the optimum effect. An initial or agent-loading construct may be used which utilizes a construct designed for rapid releasing a therapeutic agent into the tissue. This loading construct may give the tissue, in this case the atria, pulmonary arteries and vena cave a high initial dose of anti-inflammatory or other agents. After a finite period of time, the loading construct may be removed and a second construct placed which will remain after the operation. This maintenance construct may deliver the same or different agents but simply over a longer time period to sustain the effect of the agent(s) on the target tissue.

An embodiment of the device of the present invention featuring at least a macrostructure, and optionally a microstructure, may have several advantages over the prior art in providing for delivery of therapy. For example, the device of the present invention may be customizable; that is, for example, at or about the time it is to be implanted, the device may be capable of being adjusted in size and shape.

The device may be customizable or adjustable in size, in that a portion of the device may be severed (e.g., cut, sheared, torr) from the remainder, in order to achieve a device of the desired size for a particular application. The action of severing the portion from the whole does not have a negative impact upon the ability of the device to deliver a therapy, as even upon being torn, the macrostructure and microstructure largely remain intact within each portion, and may each assure extended release periods or profiles. In contrast, with prior art devices relying on a coating to ensure extended delivery release, a tear or perforation created in the coating will allow unimpeded escape of therapy from within the coating, which will negate the extended time and constant delivery rate of the therapy.

Furthermore, the device may be customizable or adjustable in shape, in that the device may be manipulated manually to conform to a target tissues surface. The presence of the macrostructure and microstructure may allow the device to be placed against a tissue or organ (whether rigid or soft), whereupon the device conforms to such a surface in order to ensure that maximum surface contact between the device and the target tissue is achieved. By ensuring that the device conforms very nearly to the surface features of the target tissue, efficient localized therapy delivery may be achieved by minimizing the opportunity for non-target tissue to be affected. The porous nature of the macrostructure and/or the microstructure may allow the uniform bending of the device without creating stress points or fractures. In contrast to rigid or elastically-rigid devices of the prior art which will be unable to easily conform to a target surface, and upon implantation would tend to leave gaps between the surface and the device where it is possible for the therapy intended for specific tissues to be inefficiently delivered or escape and affect non-target tissue away from the treatment site.

Additionally, the device of the present invention may feature a resorbable component (e.g., microstructure or macrostructure) that is capable of improving the efficiency of therapy uptake by the target cells as the component biodegrades. For example, in an embodiment where the biodegradable component features a ligand rich material (e.g. hyaluronic acid) the liberated material is able to interact with the cell membrane receptors (e.g., CD44 receptors) of the target tissue, thereby gaining entry into the cell cytoplasm, and effectively rendering the cell membrane more permeable, and more susceptible to the penetration of the therapy, thereby increasing the effectiveness of the therapy.

The device of the present invention may be able to provide a nearly constant release of at least one therapy. Alternatively, the device may feature a tailored delivery profile, and may be affected by the degradation rate of any or all of: a microstructure, a macrostructure, or the entire device. For example, the device may provide for a drug delivery cascade, wherein initially a smaller amount of therapy is released, and increases in rate of delivery as the biodegradation occurs. Alternatively, there may be a benefit in providing a large initial release of therapy, subsequently diminishing over time. These delivery profiles may be achieved by the manipulation of the material comprising the components of the device (e.g., molecular weights, therapy binding affinities, etc.), and the manner of constructing the device (e.g., pore size and shape, wall thickness, level of interconnectivity of the pores, etc.).

Thus since the invention disclosed herein may be embodied in other specific forms without departing from the spirit or general characteristics thereof, some of which forms have been indicated, the embodiments described herein are to be considered in all respects illustrative and not restrictive. The scope of the invention is to be indicated by the appended claims, rather than by the foregoing description, and all changes which come within the meaning and range of equivalency of the claims are intended to be embraced therein.

We claim:

1. A device for implant in a living being, said device comprising:
    a porous, resorbable construct having a body terminating in an agent delivery surface arranged to deliver at least one therapeutic agent to target tissue in contact with said agent delivery surface, the body comprising an open porous macrostructure that, at least at a time of implantation, is customizable in size by at least one of compressing, severing, stretching, or connecting to another of said device;
    a filament having at least one end arranged to extend out of the living being; and
    a delivery tube comprising a proximal end, a distal end, and at least two lumens extending therebetween, wherein one lumen comprises a delivery lumen and another lumen comprises a lumen for said filament, wherein said filament extends within said deliver tube and releasably attaches said distal end of said delivery tube to said porous construct.

2. The device of claim 1, further comprising a connector port, and wherein said delivery tube attaches to said porous construct at said connector port.

3. The device of claim 2, wherein said connector port comprises a groove, and at least a portion of said filament lies in said groove.

4. The device of claim 1, further comprising a connector, and wherein said proximal end of said delivery tube is attached to said, connector.

5. The device of claim 4, wherein said connector lies outside of the living being.

* * * * *